United States Patent
Daniels

(10) Patent No.: US 11,872,403 B2
(45) Date of Patent: Jan. 16, 2024

(54) SYSTEMS, METHODS, AND APPARATUS FOR EXTERNAL CARDIAC PACING

(71) Applicant: Solo Pace Inc., San Rafael, CA (US)

(72) Inventor: David V. Daniels, Burlingame, CA (US)

(73) Assignee: Solo Pace Inc., San Rafael, CA (US)

( * ) Notice: Subject to any disclaimer, the term of this patent is extended or adjusted under 35 U.S.C. 154(b) by 0 days.

(21) Appl. No.: 17/739,893

(22) Filed: May 9, 2022

(65) Prior Publication Data
US 2023/0042385 A1    Feb. 9, 2023

Related U.S. Application Data

(60) Provisional application No. 63/268,498, filed on Feb. 25, 2022, provisional application No. 63/230,064, filed on Aug. 6, 2021.

(51) Int. Cl.
*A61N 1/37*    (2006.01)
*A61B 5/363*   (2021.01)
*G16H 40/67*   (2018.01)

(52) U.S. Cl.
CPC .......... *A61N 1/3706* (2013.01); *A61B 5/363* (2021.01); *A61N 1/371* (2013.01); *G16H 40/67* (2018.01)

(58) Field of Classification Search
CPC ..... A61N 1/3625; A61N 1/371; A61F 2/2427; A61F 2/2493; A61F 2/2472;
(Continued)

(56) References Cited

U.S. PATENT DOCUMENTS 5,304,209 A * 4/1994 Adams ............... A61N 1/37217
                                                  607/30
6,711,436 B1   3/2004 Duhaylongsod
(Continued)

FOREIGN PATENT DOCUMENTS

CA    2541028 A1    9/2006
CA    2576978 C     7/2009
(Continued)

OTHER PUBLICATIONS

International Search Report and Written Opinion issued in International Application No. PCT/US2022/038192 dated Oct. 28, 2022 (18 pages).

*Primary Examiner* — George R Evanisko
(74) *Attorney, Agent, or Firm* — Bookoff McAndrews, PLLC

(57) ABSTRACT

Systems and methods for cardiac pacing during a procedure are disclosed and may include an external pulse generator (EPG) for connecting to a lead. A remote-control module (RCM) wirelessly connected to the EPG may include user inputs to control the EPG. A central processing unit (CPU) with a memory unit for storing code and a processor for executing the code may be included where the CPU is connected to the EPG and RCM. The code may control the EPG in response to user input from the RCM. The CPU may be disposed in the EPG or the RCM, or an interface module (IM) configured to communicate between an otherwise conventional EPG and the RCM. The executable code may perform a continuity test (CT) routine, a capture check (CC) routine, rapid pacing (RP) routine, and/or a back-up pacing (BP) routine, in response to user input from the RCM.

18 Claims, 20 Drawing Sheets

(58) Field of Classification Search
CPC .......... A61B 2017/00044; A61B 2017/00256; A61B 2017/00243; A61B 2017/0243
See application file for complete search history.

(56) References Cited

U.S. PATENT DOCUMENTS

| | | | |
|---|---|---|---|
| 7,187,453 B2 | 3/2007 | Belleville | |
| 7,259,862 B2 | 8/2007 | Duplain | |
| 7,265,847 B2 | 9/2007 | Duplain et al. | |
| 7,277,752 B2* | 10/2007 | Matos | A61B 5/7445 607/30 |
| 7,689,071 B2 | 3/2010 | Belleville et al. | |
| 7,759,633 B2 | 7/2010 | Duplain et al. | |
| 8,317,715 B2 | 11/2012 | Belleville et al. | |
| 8,555,712 B2 | 10/2013 | Narvaez et al. | |
| 8,752,435 B2 | 6/2014 | Belleville et al. | |
| 8,936,401 B2 | 1/2015 | Belleville et al. | |
| 9,052,466 B2 | 6/2015 | Belleville et al. | |
| 9,405,075 B2 | 8/2016 | Belleville et al. | |
| 9,405,078 B2 | 8/2016 | Belleville et al. | |
| 9,949,646 B2 | 4/2018 | Belleville | |
| 9,968,260 B2 | 5/2018 | Belleville | |
| 10,082,437 B2 | 9/2018 | Duplain et al. | |
| 10,154,787 B2 | 12/2018 | Belleville | |
| 10,173,052 B2 | 1/2019 | Daniels et al. | |
| 10,349,840 B2 | 7/2019 | Belleville et al. | |
| 10,449,378 B2 | 10/2019 | Kaib et al. | |
| 10,702,162 B2 | 7/2020 | Belleville | |
| 10,750,949 B2 | 8/2020 | Belleville | |
| 10,758,725 B2 | 9/2020 | Daniels et al. | |
| 10,881,851 B2 | 1/2021 | Daniels et al. | |
| D921,003 S | 6/2021 | Lalancette et al. | |
| D921,648 S | 6/2021 | Lalancette et al. | |
| 11,045,318 B2 | 6/2021 | Faurie | |
| D926,199 S | 7/2021 | Lalancette et al. | |
| 11,065,451 B1 | 7/2021 | Gross | |
| 11,369,277 B2 | 6/2022 | Belleville | |
| 2006/0133715 A1 | 6/2006 | Belleville et al. | |
| 2006/0233484 A1 | 10/2006 | Neste et al. | |
| 2010/0056858 A1 | 3/2010 | Mokelke et al. | |
| 2011/0066047 A1 | 3/2011 | Belleville et al. | |
| 2011/0208265 A1 | 8/2011 | Erickson et al. | |
| 2013/0218032 A1 | 8/2013 | Belleville | |
| 2014/0039325 A1 | 2/2014 | Belleville | |
| 2019/0224011 A1 | 7/2019 | Faurie | |
| 2020/0282204 A1 | 9/2020 | Capek et al. | |
| 2020/0289057 A1 | 9/2020 | An et al. | |
| 2020/0329972 A1 | 10/2020 | Belleville | |
| 2021/0030440 A1 | 2/2021 | Faurie | |
| 2021/0100462 A1 | 4/2021 | Belleville et al. | |
| 2021/0186696 A1 | 6/2021 | Faurie | |
| 2022/0175256 A1 | 6/2022 | Lalancette et al. | |
| 2022/0192520 A1 | 6/2022 | Lalancette et al. | |
| 2022/0248969 A1 | 8/2022 | Belleville | |
| 2022/0361762 A1* | 11/2022 | Lalancette | A61B 5/6851 |

FOREIGN PATENT DOCUMENTS

| | | |
|---|---|---|
| CA | 2721282 C | 10/2011 |
| CA | 2808202 C | 11/2013 |
| CA | 2591787 C | 1/2016 |
| CA | 2787534 C | 5/2016 |
| CA | 2819564 C | 1/2017 |
| CA | 2999071 A1 | 3/2017 |
| CA | 2912907 C | 11/2017 |
| CA | 2848728 C | 6/2018 |
| CA | 2912904 C | 6/2018 |
| CA | 3095596 A1 | 10/2019 |
| CA | 3103694 A1 | 1/2020 |
| CA | 3140414 A1 | 11/2020 |
| CA | 3140416 A1 | 11/2020 |
| CN | 100451694 C | 1/2009 |
| CN | 103534568 A | 1/2014 |
| CN | 103959114 A | 7/2014 |
| CN | 103328033 B | 5/2016 |
| CN | 108027294 B | 5/2020 |
| CN | 112262377 A | 1/2021 |
| CN | 113874062 A | 12/2021 |
| CN | 114096301 A | 2/2022 |
| CN | 114302673 A | 4/2022 |
| EP | 1834164 A4 | 5/2011 |
| EP | 2408356 A1 | 1/2012 |
| EP | 2637727 A4 | 4/2014 |
| EP | 1803004 B1 | 2/2015 |
| EP | 2638375 B1 | 1/2019 |
| EP | 3353517 B1 | 3/2020 |
| EP | 3141881 B1 | 5/2020 |
| EP | 3776232 A1 | 2/2021 |
| EP | 2751604 B1 | 9/2021 |
| EP | 3951459 A1 | 2/2022 |
| EP | 3968851 A1 | 3/2022 |
| EP | 3813654 A4 | 4/2022 |
| EP | 3958947 A4 | 12/2022 |
| EP | 3969096 A4 | 1/2023 |
| ES | 2539007 T3 | 6/2015 |
| ES | 2789448 T3 | 10/2020 |
| JP | 4994244 B2 | 8/2012 |
| JP | 6264172 B2 | 8/2013 |
| JP | 5591906 B2 | 9/2014 |
| JP | 5866371 B2 | 2/2016 |
| JP | 5894197 B2 | 3/2016 |
| JP | 6200423 B2 | 9/2017 |
| JP | 6351665 B2 | 7/2018 |
| JP | 2018527592 A | 9/2018 |
| JP | 6412527 B2 | 10/2018 |
| JP | 1663291 S | 7/2020 |
| JP | 1666760 S | 8/2020 |
| JP | 1674258 S | 12/2020 |
| JP | 6864655 B2 | 4/2021 |
| JP | 2021107935 A | 7/2021 |
| JP | 2021520260 A | 8/2021 |
| JP | 2021529015 A | 10/2021 |
| JP | 2022000647 A | 1/2022 |
| JP | 2022529514 A | 6/2022 |
| JP | 2022532668 A | 7/2022 |
| JP | 2022533646 A | 7/2022 |
| PT | 3353517 T | 5/2020 |
| WO | 2006032128 A1 | 3/2006 |
| WO | 2006058423 A1 | 6/2006 |
| WO | 2006066393 A1 | 6/2006 |
| WO | 2010105356 A1 | 9/2010 |
| WO | 2011088572 WO | 7/2011 |
| WO | 2012061935 A1 | 5/2012 |
| WO | 2012119237 A1 | 9/2012 |
| WO | 2013029157 A1 | 9/2012 |
| WO | 2017049392 A1 | 3/2017 |
| WO | 2019195323 A1 | 10/2019 |
| WO | 2020000102 A1 | 1/2020 |
| WO | 2020219457 A1 | 10/2020 |
| WO | 2020236492 A1 | 11/2020 |
| WO | 2020236494 A1 | 11/2020 |

* cited by examiner

SYSTEMS, METHODS, AND APPARATUS FOR EXTERNAL CARDIAC PACING

CROSS-REFERENCE TO RELATED APPLICATIONS

This application claims the benefit of U.S. Provisional Patent Application 63/230,064, filed Aug. 6, 2021, and U.S. Provisional Patent Application 63/268,498, filed Feb. 25, 2022, the entire contents of each of which are incorporated herein by reference.

FIELD

The present disclosure generally relates to external cardiac pacing devices and methods.

BACKGROUND

External pulse generators are used in a variety of clinical applications such as cardiac pacing in transcatheter heart valve (THV) replacement procedures, most commonly in current clinical practice, transcatheter aortic valve replacement (TAVR). In this application, the heart may be briefly paced at an elevated rate to reduce the cardiac flow, and thus the pressure gradient, across the annulus where the artificial valve is to be deployed. In doing so, the propensity for an excessive pressure gradient to cause the artificial valve to move during deployment is mitigated, thus enabling accurate valve positioning and avoiding valve embolization. Currently, this is performed using an external pulse generator (EPG) to drive a temporary pacing wire positioned in the ventricle, for example. A third person (e.g., surgical nurse or technician) outside the sterile field manually operates the pulse generator according to verbal instructions provided by the cardiologist who is in the sterile field monitoring the patient and attending to valve delivery and deployment. The use of a third party to manually operate the EPG based on verbal instructions is susceptible to human error, both in communication and execution, potentially introducing unnecessary risk to the procedure.

SUMMARY

To mitigate such risk, the present disclosure describes systems and methods for the cardiologist to directly control the pacing activity by placing pacing control features in close proximity to the cardiologist, e.g., in the sterile field, thus eliminating the need for a third person and the need for verbal commands. In addition, the present disclosure describes systems and methods that have a level of automation, replacing some of the manual control of the external pulse generator with automatic algorithms.

One example embodiment provides a system for assisted pacing during a cardiac procedure such as a TAVR procedure. The system may include an external pulse generator (EPG) configured for connection to a lead such as a guidewire. The system may also include a remote-control module (RCM) wirelessly connected to the EPG, wherein the RCM includes user inputs configured to control the EPG. To facilitate connection to a guidewire with at least a partial insulative outer portion, the system may include a guidewire connector configured to penetrate the insulative outer portion to establish electrical communication with the guidewire. The system may include a central processing unit (CPU) with a memory unit for storing code and a processor for executing the code, wherein the CPU is operably connected to the EPG and RCM. The code may include instructions to assist in control of the EPG based on user input from the RCM. The CPU may be disposed in the EPG or the RCM, or an interface module (IM) configured to communicate between an otherwise conventional EPG and the RCM.

The code may include instructions to perform a continuity test (CT) routine, a capture check (CC) routine, rapid pacing (RP) routine, and/or a back-up pacing (BP) routine, all based on user input from the RCM.

The CC routine may include the steps of waiting for a user readiness input from the RCM, ramping up a paced pulse rate (PPR) from the EPG, determining if a sensed heart-rate (HR) is the same as the PPR, and triggering an indicator indicative of 1:1 capture. The CC routine may further include an automatic rate determination and ramp-up subroutine. The CC routine may further include a manual capture rate determination and ramp-up or ramp-down subroutine. The CC routine may further include a capture verification subroutine. The capture verification subroutine may monitor PPR and/or HR over a period corresponding to at least one respiratory cycle.

The RP routine may include the steps of waiting for a user readiness input from the RCM, ramping up a pacing output from the EPG, and triggering an indicator when the PPR or HR is suitable for valve deployment. The RP routine may further include an automatic ramp up subroutine and an automatic ramp down subroutine. The amplitude of the pacing output may be higher in the RP routine than the amplitude in the CC routine.

The BP routine may include the steps of waiting for a user readiness input from the RCM, ramping down the PPR from the EPG, determining if a HR is inhibited due to the detection of an intrinsic heart beat prior to the pace pulse would otherwise be delivered (in VVI mode), and triggering an indicator indicative of inhibition. In the presence of intrinsic abnormal bradycardia from heart block or other pathological causes, the EPG may ramp up PPR to a normal HR to stabilize the patient's hemodynamics.

Another example embodiment provides a method for assisted pacing during a cardiac procedure such as a TAVR procedure. The method may include the steps of connecting an external pulse generator (EPG) to a lead or guidewire, connecting a remote-control module (RCM) to the EPG via a wireless connection, activating a computer executable code based on a user input from the RCM, and executing code instructions to perform assisted pacing based on user input from the RCM. Executing the instructions may include steps to perform a continuity test (CT) routine, a capture check (CC) routine, rapid pacing (RP) routine, and/or a back-up pacing (BP) routine, all based on user input from the RCM, as described above.

Another example embodiment disclosed herein provides a system for cardiac pacing. The system may include an EPG configured to connect to a lead and to provide pacing outputs; an RCM may be wirelessly connected to the EPG, wherein the RCM may be configured to receive user inputs and to control the EPG; and a CPU that may be operably connected to the EPG and RCM, the CPU may be configured to execute code, wherein the code may include instructions to perform a (RP routine in response to a first user input received at the RCM, the RP routine may include: receiving a user readiness input from the RCM; modifying a PPR of a pacing output from the EPG in response to the user readiness input; determining if the modified PPR meets a predetermined setting; and triggering an indicator if the modified PPR meets the predetermined setting.

Aspects of the disclosed system for cardiac pacing may include one or more of the following features: the RP routine may further include an automatic PPR ramp up subroutine; the code may further include instructions to perform a CT routine, the CT routine may include: determining that the lead is connected to the EPG and triggering an indicator in response to determining that the lead is connected to the EPG; disabling one or more accessory buttons in response to determining that the lead is connected to the EPG; the code may further include instructions to perform a CC routine in response to a second user input received at the RCM, the CC routine may include: receiving the user readiness input from the RCM, ramping up the PPR of the pacing output from the EPG to a ramped up PPR in response to receiving the user readiness input, determining if a sensed heart-rate (HR) is approximately the same as the ramped up PPR, and triggering an indicator indicative of a 1:1 capture in response to determining if the sensed HR is approximately the same as the ramped up PPR of the pacing output; the CC routine may further include an automatic rate determination subroutine; the CC routine may further include at least one of a manual capture rate determination subroutine or a capture verification subroutine; the capture verification subroutine may monitor capture over a period of at least one respiratory cycle; the code may further include instructions to perform a BP routine in response to a second user input received at the RCM, the BP routine may include: receiving the user readiness input from the RCM, ramping down the PPR from the EPG in response to receiving the user readiness input, determining if a heart-rate (HR) is inhibited, and triggering an indicator indicative of inhibition in response to determining if the HR is inhibited; the EPG may be a non-sterile component and the RCM may be a sterile component; the EPG may be configured to transmit pacing output information to a lab display; the EPG may be configured to operate in either unipolar or bipolar modes of operation; the EPG may be further configured for connection to a grounding pad; the EPG may be configured to receive sensing signals from the lead; the EPG may be configured to receive an electrocardiogram (ECG) signal; the lead may include a guidewire with at least a partial insulative outer portion; a guidewire connector may be connected to the EPG via a cable, wherein the guidewire connector may be configured to penetrate the partial insulative outer portion to establish electrical communication with the guidewire; the CPU may be disposed in the EPG or the RCM; an interface module (IM) may facilitate communication between the EPG and RCM; and the CPU may be disposed in the IM.

Another example embodiment disclosed herein provides a method of cardiac treatment (e.g., pacing). The method may include connecting an EPG to a guidewire; connecting an RCM to the EPG; executing first code instructions to perform an RP routine to modify a PPR of a pacing output from the EPG in response to a first user input from the RCM; and triggering an indicator when the PPR reaches a predetermined setting for valve deployment.

Aspects of the disclosed method may include one or more of the following features: the RP routine may include receiving a user readiness input from the RCM; modifying a PPR of a pacing output from the EPG in response to the user readiness input; and determining if the PPR meets the predetermined setting for valve deployment based on modifying the PPR; deploying a valve in response to determining if the PPR meets the setting for valve deployment; executing second code instructions to perform a CT routine, where the CT routine may include: determining that the guidewire is connected to the EPG and triggering an indicator in response to determining that the guidewire is connected to the EPG; executing second code instructions to perform a CC routine in response to a second user input from the RCM, where the CC routine may further include: receiving a user readiness input from the RCM, ramping up the PPR of the pacing output from the EPG to a ramped up PPR, determining if a sensed heart-rate (HR) is approximately the same as the ramped up PPR, and triggering an indicator indicative of a 1:1 capture in response to determining if the sensed HR is approximately the same as the ramped up PPR of the pacing output; and executing second code instructions to perform a BP routine in response to a second user input from the RCM, where the BP routine may include: receiving a user readiness input from the RCM, ramping down the PPR from the EPG in response to the user readiness input, determining if a heart-rate (HR) is inhibited, and triggering an indicator indicative of inhibition in response to determining if the HR is inhibited.

Another example embodiment disclosed herein includes a system for cardiac pacing. The system may include an EPG configured to connect to a lead and to provide pacing outputs; an RCM operably connected to the EPG, wherein the RCM is configured to receive user inputs and to control the EPG in response to the user inputs; and a processor in communication with the EPG and RCM, the processor configured to transmit signals to the EPG to perform at least one of RP routine, a CT routine, a CC routine, or a BP routine.

Aspects of the disclosed system for cardiac pacing may include one or more of the following features: the RP routine may include: receiving a user readiness input from the RCM, modifying a PPR of a pacing output from the EPG in response to receiving the user readiness input, determining if the modified PPR meets a setting for valve deployment, and triggering an indicator if the PPR meets the setting for valve deployment; the CT routine may include: determining that the lead is connected to the EPG and triggering an indicator in response to determining that the lead is connected to the EPG; the CC routine may include: receiving a user readiness input from the RCM, ramping up a PPR of the pacing output from the EPG to a ramped up PPR in response to receiving the user readiness input, determining if a sensed heart-rate (HR) is approximately the same as the ramped up PPR, and triggering an indicator indicative of a 1:1 capture in response to determining if the sensed HR is approximately the same as the ramped up PPR of the pacing output; and the BP routine may include: receiving a user readiness input from the RCM, ramping down a PPR from the EPG in response to receiving the user readiness input, determining if a heart-rate (HR) is inhibited, and triggering an indicator indicative of inhibition in response to determining if the HR is inhibited.

The above summary is not intended to describe each and every embodiment or implementation of the present disclosure.

BRIEF DESCRIPTION OF THE FIGURES

The accompanying drawings, which are incorporated into and constitute a part of this specification, illustrate various exemplary embodiments and, together with the description, serve to explain the principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements, other than those specifically shown, are contemplated and are within the scope of the present disclosure.

There are many inventions described and illustrated herein. The described inventions are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment(s).

The drawings illustrate example embodiments of the present disclosure and, along with the description, serve to explain the principles of the disclosure. The drawings are only illustrative of certain embodiments and do not limit the disclosure or invention.

Figure 1A:
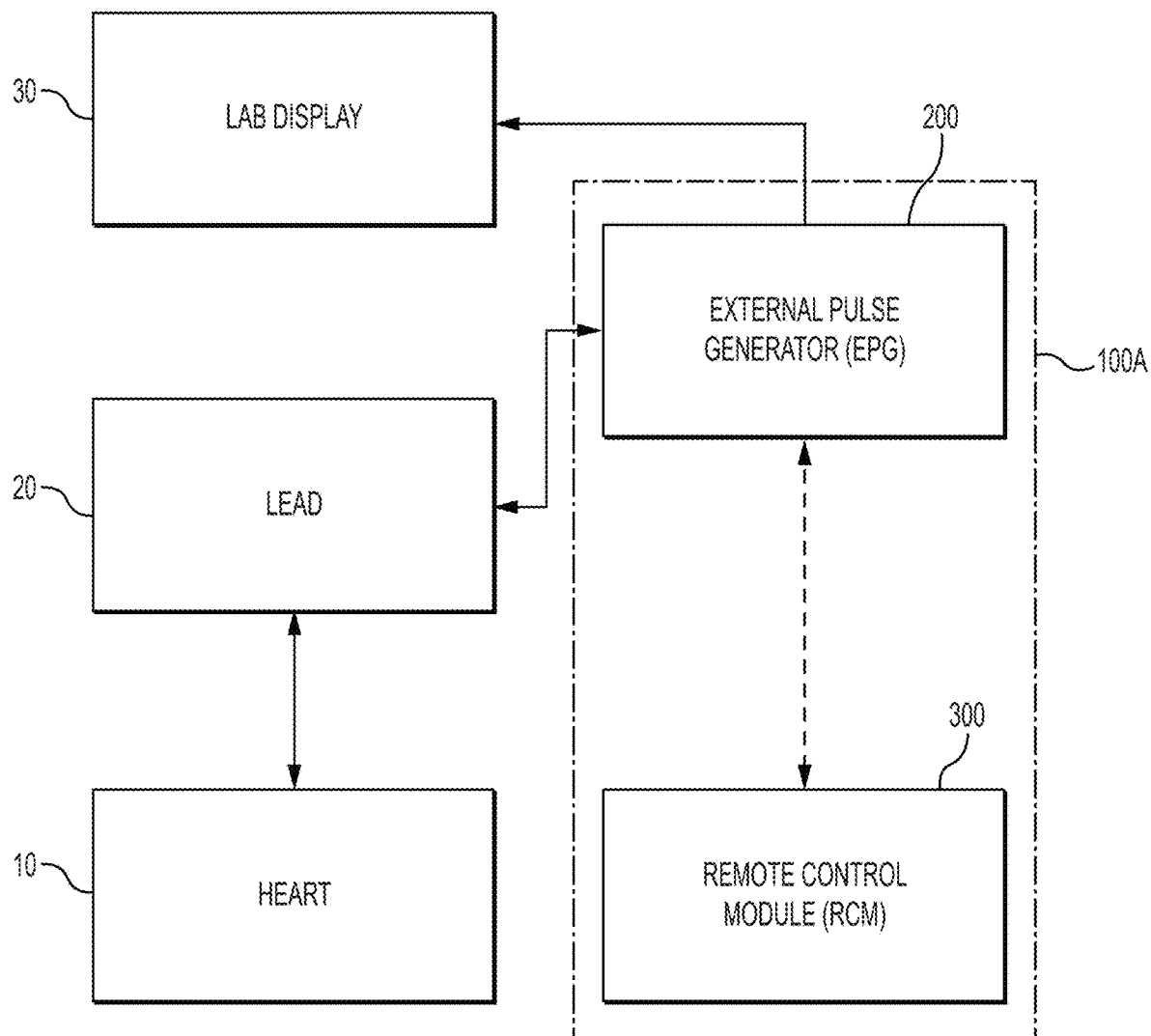
Figure 1B:
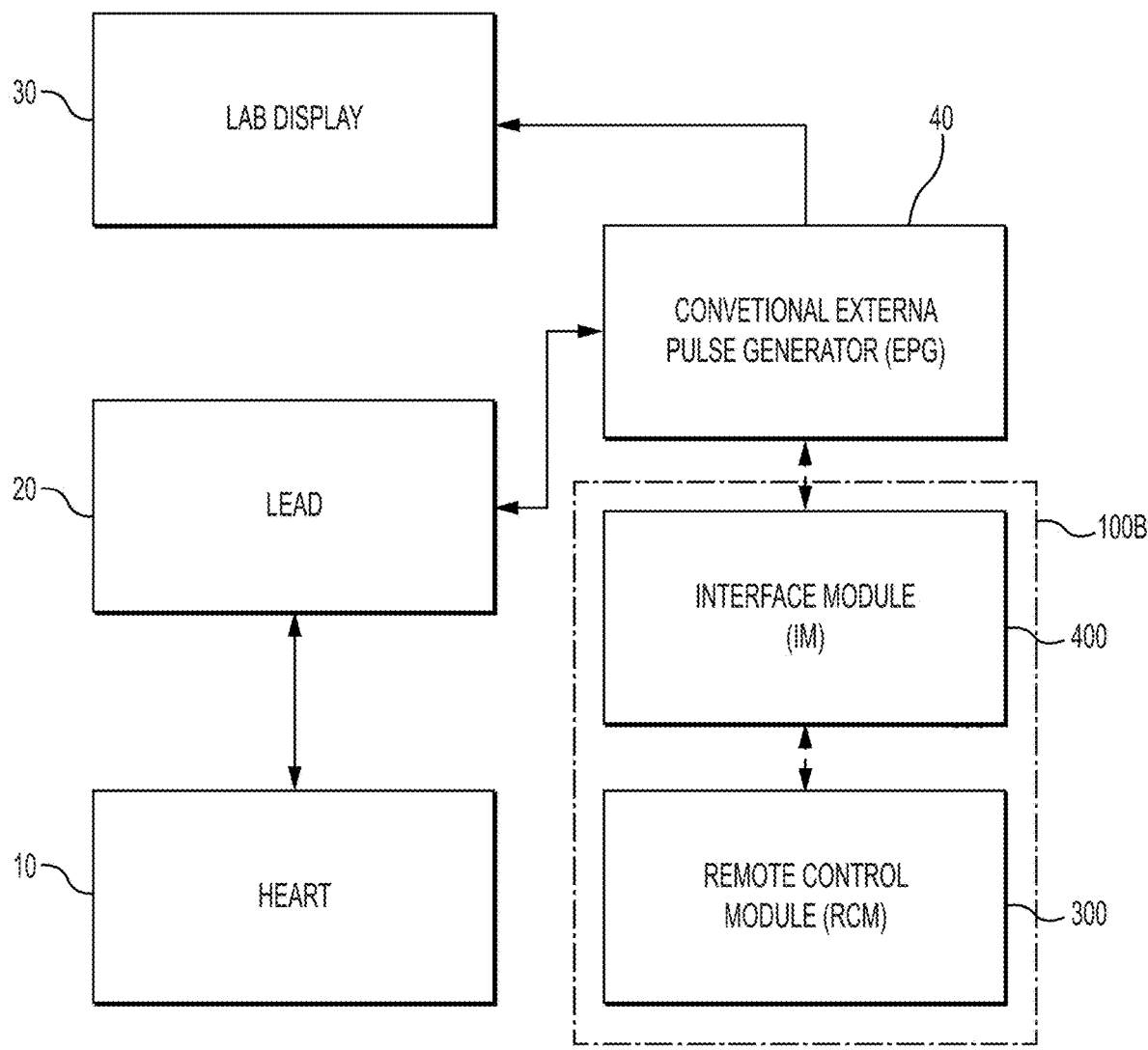
Figure 1C:
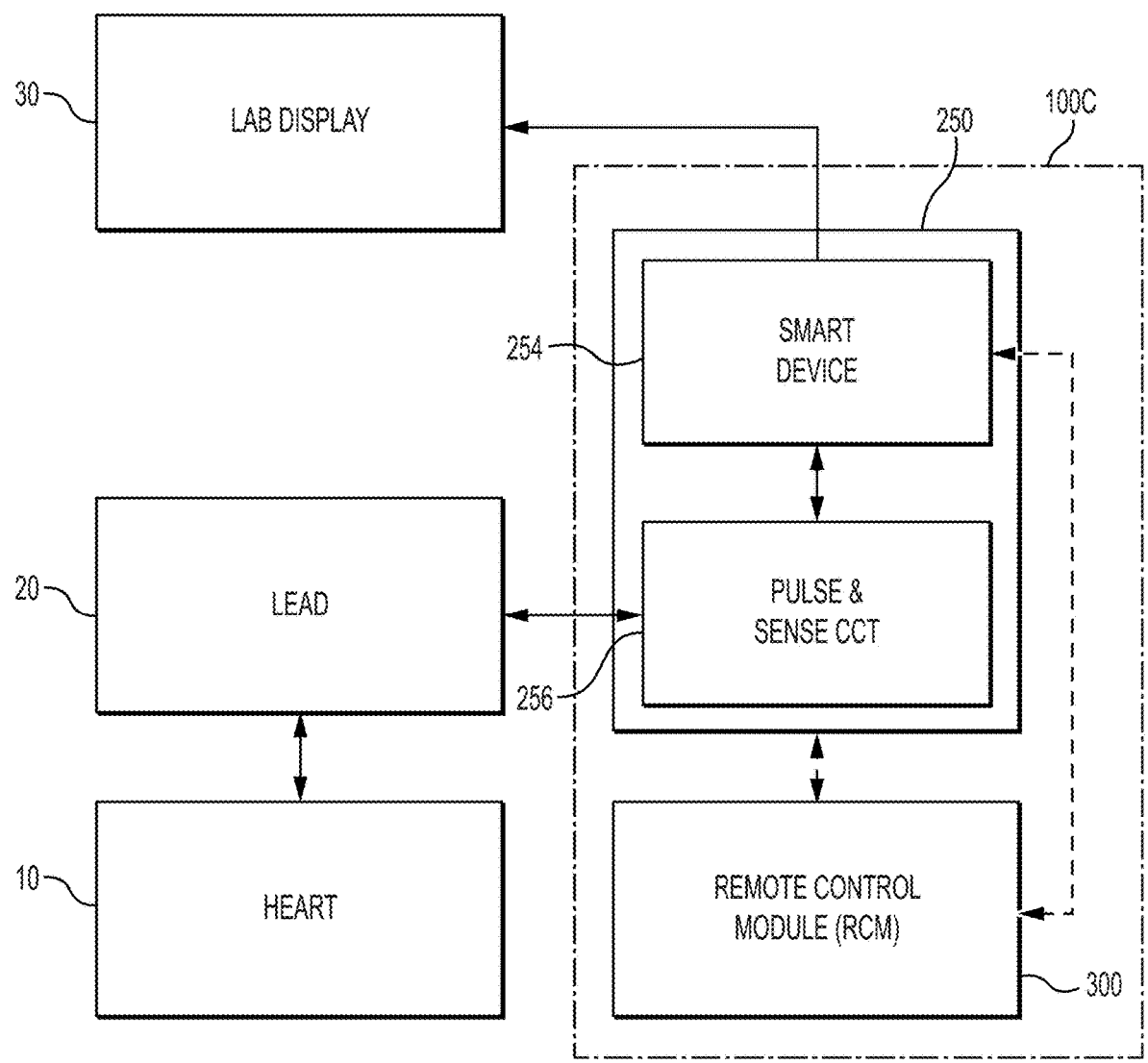
Figure 2:
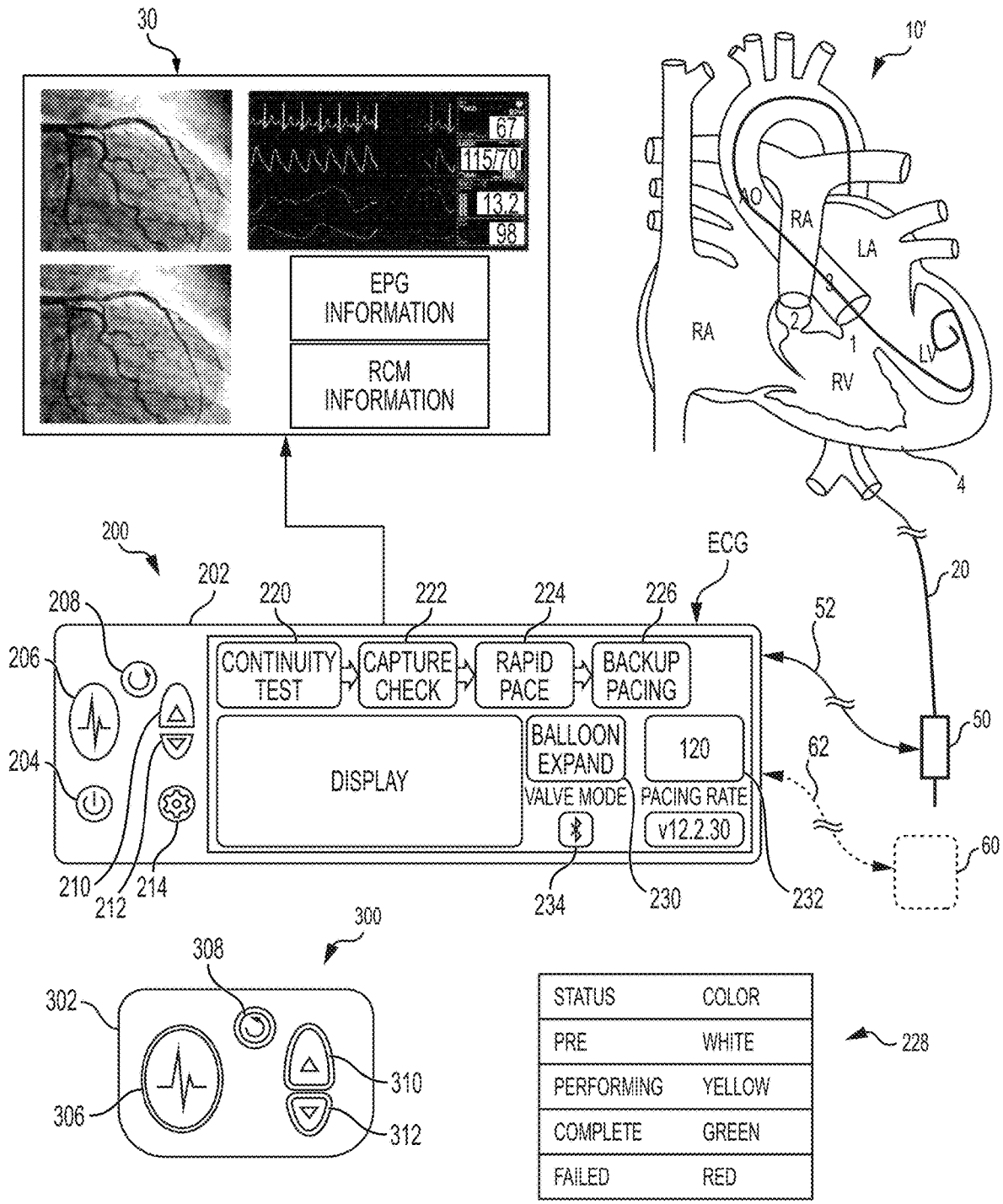
Figure 3A:
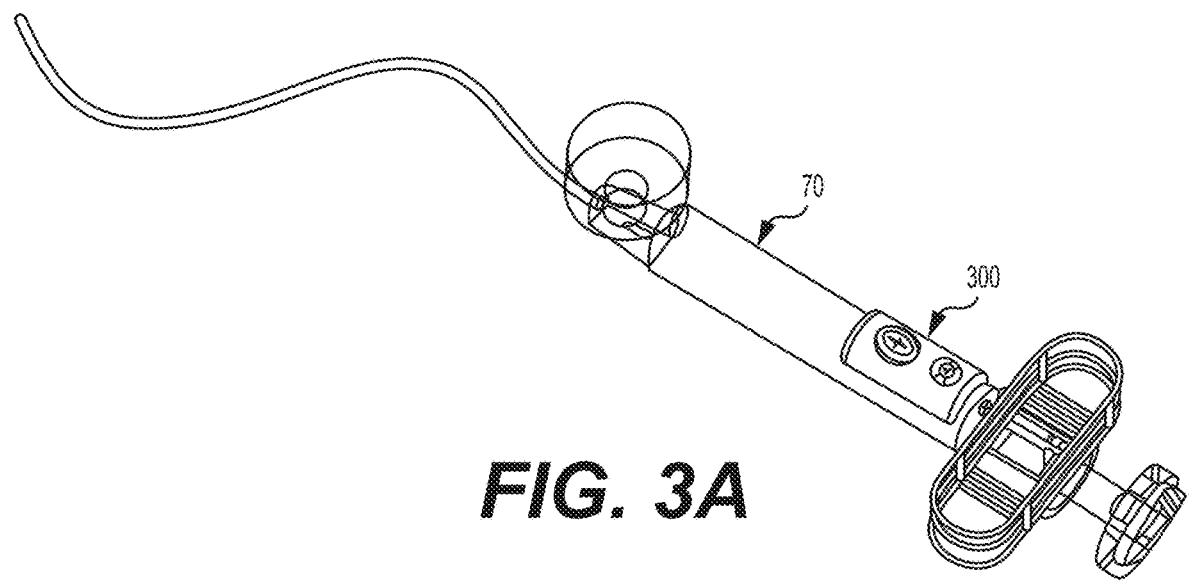
Figure 3B:
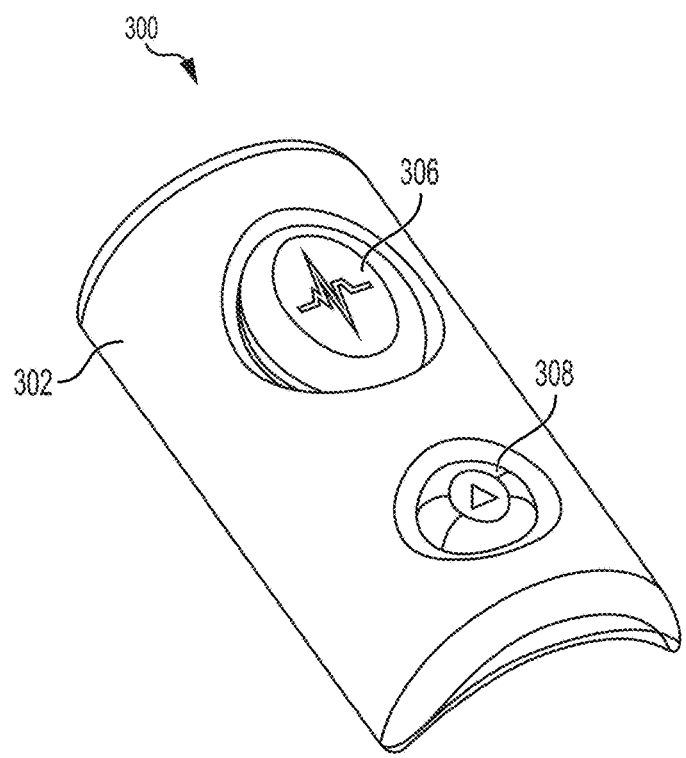
Figure 4A:
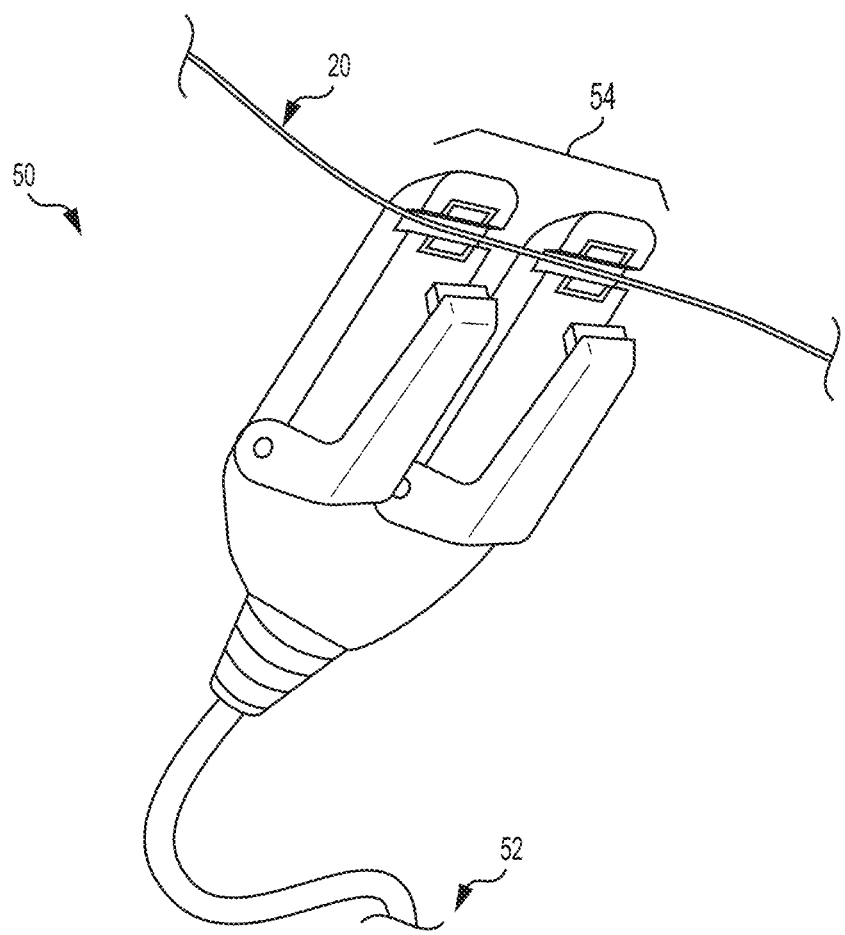
Figure 4B:
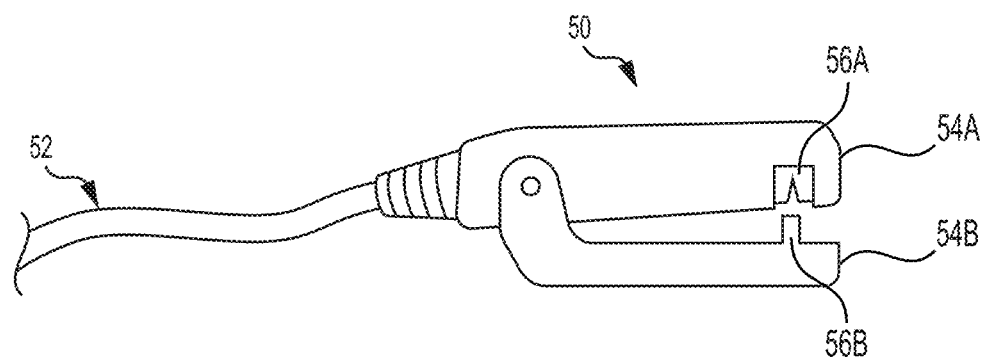
Figure 5:
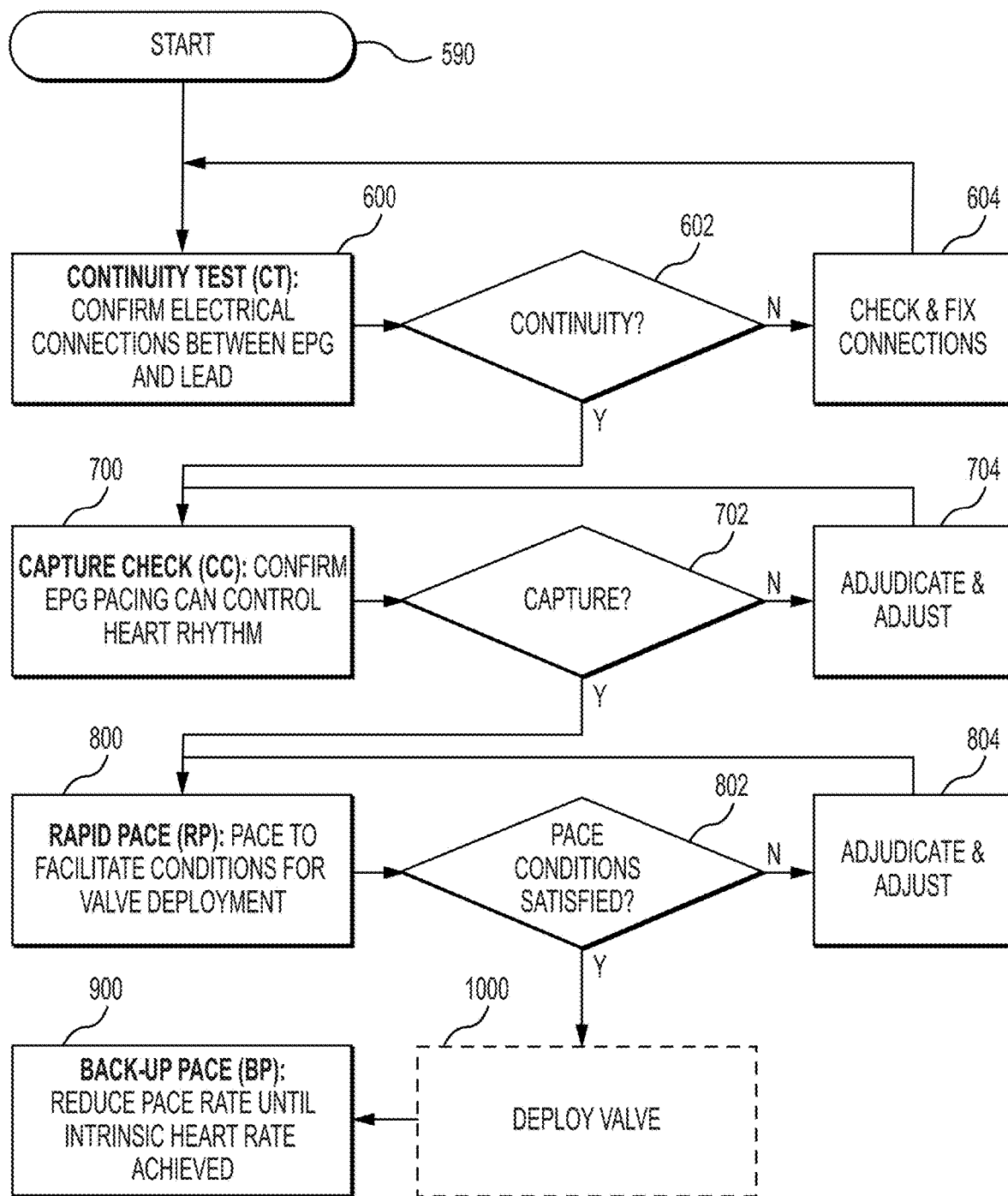
Figure 6:
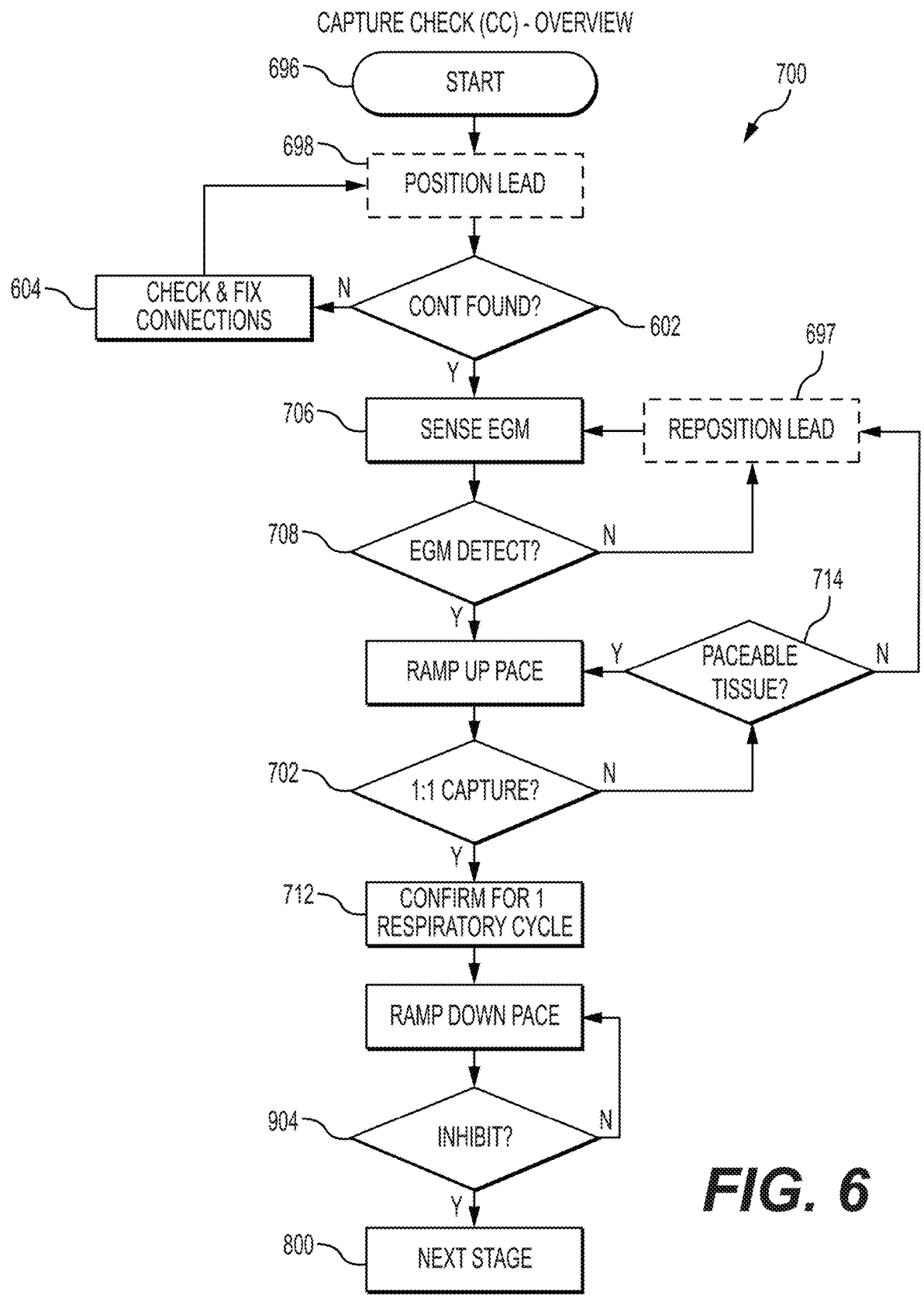
Figure 7:
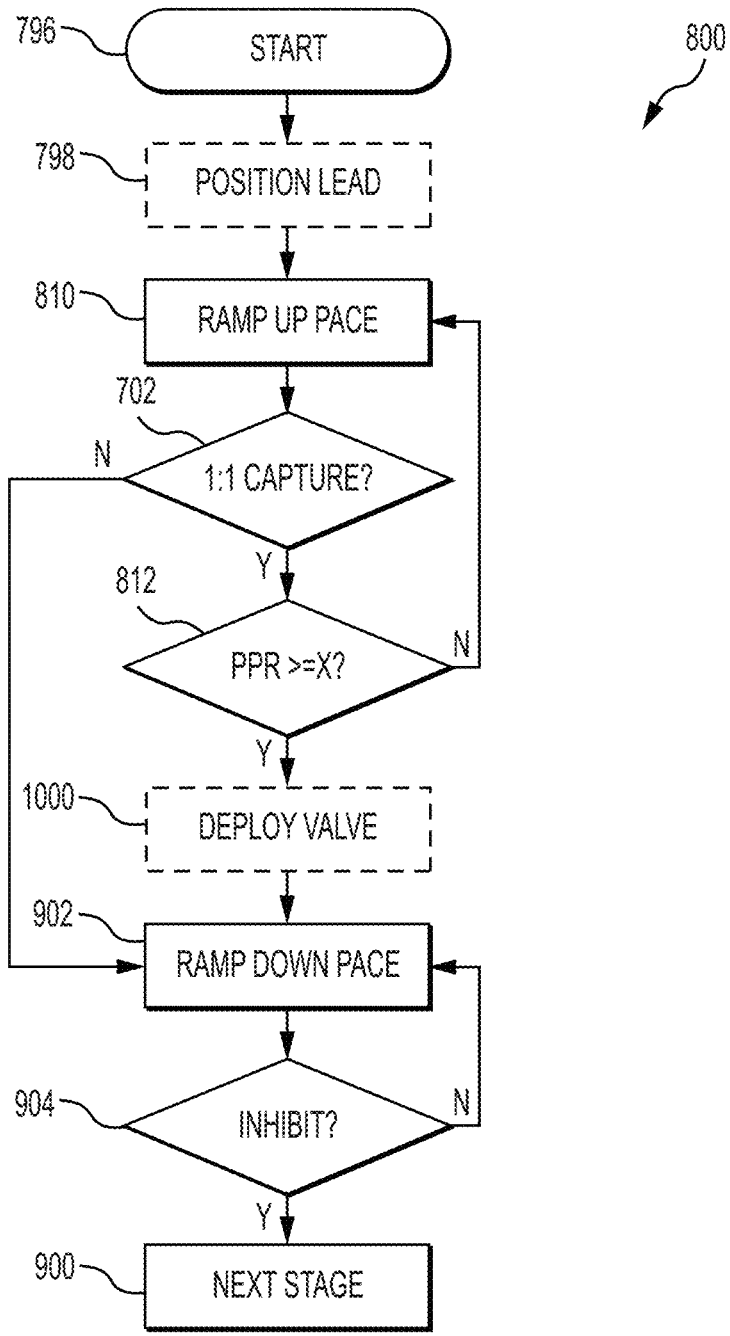

FIG. 1A is a schematic block diagram of a pacing assist system for use in a cardiac procedure such as TAVR, according to an example embodiment of the present disclosure;

FIG. 1B is a schematic block diagram of a pacing assist system, according to an alternative example embodiment of the present disclosure;

FIG. 1C is a schematic block diagram of a pacing assist system, according to another alternative example embodiment of the present disclosure;

FIG. 2 is a schematic illustration from a user's perspective of the pacing assist system shown in FIG. 1A, according to an example embodiment of the present disclosure;

FIGS. 3A and 3B are schematic illustrations of an alternative remote-control module for use in the system shown in FIG. 2;

FIGS. 4A and 4B are schematic illustration of a guidewire connector shown in perspective and side views, respectively, according to an example embodiment of the present disclosure;

FIG. 5 is a schematic flow chart of example operational stages for use in the systems shown in FIGS. 1A, 1B and 1C, according to an embodiment of the present disclosure;

FIG. 6 is a schematic flow chart showing an example overview of the capture check process as generally described with reference to FIG. 5;

FIG. 7 is a schematic flow chart showing an example overview of the rapid pacing process as generally described with reference to FIG. 5; and FIGS. 8, 9, 10A, 10B, 11A, 11B, 11C, 11D, 12A, 12B, and 13 are schematic flow charts showing detailed examples of the processes generally described with reference to FIG. 5.

While embodiments of the disclosure are amenable to various modifications and alternative forms, specifics thereof have been shown by way of example in the drawings and will be described in some detail. It should be understood, however, that the intention is not to limit the disclosure to the particular embodiments described. On the contrary, the intention is to cover all modifications, equivalents, and alternatives falling within the spirit and scope of the invention.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish an element or a structure from another. Moreover, the terms "a" and "an" herein do not denote a limitation of quantity, but rather denote the presence of one or more of the referenced items.

The term "distal end," or any variation thereof, refers to the portion of a device farthest from an operator of the device during a procedure. Conversely, the term "proximal end," or any variation thereof, refers to the portion of the device closest to the operator of the device. Further, any use of the terms "around," "about," "substantially," and "approximately" generally mean +/−10% of the indicated value.

DETAILED DESCRIPTION

FIG. 1A is a schematic block diagram of a pacing assist system 100A for use in a TAVR procedure, for example, according to an example embodiment of the present disclosure. System 100A may generally include an external pulse generator 200 configured for connection to a lead 20 via a cable. External pulse generator 200 may be a temporary or single-use pulse generator. Lead 20 may be positioned with its proximal end extending out from the access sheath and its distal end in the heart 10 (e.g., left or right ventricle) to establish electrical communication between the EPG 200 and the heart 10. The connection between the EPG 200 and lead 20 may be bidirectional to facilitate pacing and EGM (intracardiac electrocardiogram) sensing.

System 100A may also generally include a remote-control module (RCM) 300 connected to the EPG 200 and configured to control pacing output from the EPG 200 based on user input from the cardiologist. RCM 300 may be connected to the EPG 200 via a wireless connection (e.g., Bluetooth) or a hard wired connection (e.g., extended cable). The connection between the RCM 300 and the EPG 200 may also be bidirectional such that the RCM 300 may issue command signals to the EPG 200, and the EPG 200 may issue status signals to the RCM 300. In use, the EPG 200 may be placed outside the sterile field, whereas the RCM 300 may be placed proximate the hands of the cardiologist inside the sterile field.

Lead 20 may be unipolar or bipolar. If unipolar, EPG 200 may also be configured for connection to a grounding pad (not shown). Lead 20 may comprise a conventional guidewire that is unipolar or a specialty temporary pacing guidewire (e.g., Wattson®, Teleflex, Inc.) that is bipolar. Those of ordinary skill will also recognize that any suitable lead may be used in conjunction with the principles of the present disclosure. If a conventional guidewire is used for lead 20, a guidewire connector (not shown) may be provided to facilitate an electrical connection thereto. Because conventional guidewires often have an insulative outer surface (e.g., Teflon® coating), the guidewire connector may be configured to penetrate the insulation to achieve an electrical connection to the metal (e.g., 304 v stainless steel) portion of the guidewire.

Output from the EPG 200 may be connected to a conventional lab display 30 (such as the C-View® Large Display from Carrot Medical). Examples of information shown on display 30 may include static and/or cine views of the heart, intracardiac EGM, ECG, heart rate, respiratory rate and other physiologic or hemodynamic data. Additionally, a complete or partial mirror representation of the display information on the EPG 200 and/or RCM 300 may be shown on the display 30. For example, pacing waveform, pulse rate, pulse amplitude, pulse width and other pacing data, stage indicators, status and readiness indicators, procedural notes and instructions, etc.

FIG. 1B is a schematic block diagram of an alternative pacing assist system 100B according to an alternative example embodiment of the present disclosure. In this embodiment, a conventional EPG 40 may be employed. To facilitate connection and control between the conventional EPG 40 and the RCM 300, an interface module (IM) 400 be used. The IM 400 may be connected to the IPG 40 by hard wire, for example, and reside outside the sterile field. The IM 400 may be wirelessly connected to the RCM 300 residing inside the sterile field adjacent the cardiologist's hands. The IM 400 may be configured to function in the same or similar manner as EPG 200, absent the pulse engine and associated pacing outputs. In other words, the IM 400 assumes command and control of the conventional EPG 40: the IM 400 becomes the master; and the conventional EPG 40 becomes the slave. The connections between the RCM 300, IM 400 and EPG 40 may be bidirectional such that the RCM 300 may issue command signals to the IM 400 which are translated to the EPG 40. Similarly, the EPG 40 may issue status signals to the IM 400 which are translated to the RCM 300.

FIG. 1C is a schematic block diagram of an alternative pacing assist system 100C according to an alternative example embodiment of the present disclosure. In this embodiment, an alternative EPG 250 configuration may be employed, wherein the EPG may include a smart device 254 and a pulse generator/sensing circuit 256. The smart device 254 may comprise a conventional smart phone, tablet, etc., for example, which typically contain input/output (I/O), display, wireless communication, power, processor and memory features. When combined with a pulse engine and sensing circuit 256, EPG 250 may be configured to have the same functionality as EPG 200 and may be operated in a similar fashion. The EPG 250 may reside outside the sterile field, for example, and may be directly connected to the lead 20 via pulse and sensing circuit 256, directly connected to the lab display 30 via smart device 254, and wirelessly connected to the RCM 300 via smart device 254.

As will be described in more detail herein, systems 100A, 100B, and 100C may incorporate a central processing unit (CPU) with a memory unit for storing code and a processor for executing the code. The CPU may be operably connected to the RCM 300 and the EPG 200 in system 100A, to the RCM 300 and IM 400 in system 100B, or the RCM 300 and the smart device 254 in EPG 250 in system 100C. The CPU may be disposed in the EPG 200, the EPG 250, the RCM 300, or the IM 400. According to an embodiment, the CPU may be a cloud component operably connected to the RCM 300 and/or EPG 200 via a network connection. In this embodiment, the CPU may receive data from EPG 200 and/or RCM 300 and may transmit signals to EPG 200 and/or RCM 300 (e.g., over the network connection). The executable code may include instructions to control the EPG 200, 250, or 40 based on user input from the RCM 300. As used hereinafter, systems 100A, 100B, and 100C may be referred to collectively as system 100.

FIG. 2 is a schematic illustration from a user's perspective of the pacing assist system 100A shown in FIG. 1A, according to an example embodiment of the present disclosure. In this example embodiment, the heart 10 may be paced via a guidewire 20 placed in the left ventricle (LV), for example. A valve delivery system (not shown) may be delivered over the guidewire 20 to the desired location for valve deployment. In general, the pacing signal output from EPG 200 may be electrically connected to the guidewire 20 by way of a cable 52 and a guidewire connector clamp 50. As mentioned previously, the guidewire connector 50 may be configured to penetrate insulation on the guidewire 20 to achieve an electrical connection to the conductive (e.g., metal) portion of the guidewire 20. In this manner, the EPG 200 may be electrically coupled to intracardiac tissue of the heart 10 for purposes of pacing and sensing (EGM).

Also as mentioned previously, a bipolar guidewire 20 may be used for bipolar pacing. Examples of bipolar configurations are described in U.S. Pat. Nos. 10,173,052; 10,758,725; 10,881,851; and 11,045,318, the entire disclosures of which are incorporated herein by reference. Alternatively, a conventional guidewire 20 may be used for unipolar pacing, together with a grounding pad 60, also electrically connected to the EPG 200 via a cable 62. Examples of unipolar configurations are describe in U.S. Published Patent Applications Nos. 2019/0224011, 2021/0030440, and 2021/0186696, the entire disclosures of which are incorporated herein by reference.

The EPG 200 may include a number of input and output terminals (not visible) mounted to the outside of the housing 202, including pacing output terminals (anode and cathode) for connection to the guidewire 20. The pacing output terminals may also serve as sensing input terminals for sensing EGM, and/or the EPG 200 may include a separate input terminal(s) to receive an electrocardiogram (ECG). In either case, the EGM and ECG may be used to derive a cardiac wave form indicative of HR and other physiological parameters of cardiac function. The EPG 200 may also include and a ground terminal for connection to the grounding pad 60 via cable 62.

The EPG 200 may include a number of user inputs on the front of the housing 202, such as a power button 204, a primary button 206, an accessory button 208, up 210 and down 212 buttons, a settings button 214. Alternatively, or additionally, the EPG 200 may also be configured to receive user inputs via a foot actuator, a voice actuation component, or any combination of user inputs discussed herein. In addition to command-and-control inputs from the user, the EPG may be configured to receive and store settings such as patient-specific settings or physician-specific preferences for pacing parameters, rate limits, etc. The EPG 200 may further include a number of stage and status indicators such as indicators corresponding to a continuity test (CT) stage 220, a capture check (CC) stage 222, a rapid pacing (RP) stage 224, and a back-up pacing (BP) stage 226, for example. The status of each stage may be represented by illuminating a different color. For example, the various states (e.g., pre-, performing, complete, failed) may be represented by intuitive colors (e.g., white, yellow, green, red, respectfully) as shown in table 228.

The EPG 200 may be operated in different modes depending on what type of TAVR valve is being deployed (e.g., self-expanding or balloon expandable) and what type of pacing is being utilized (e.g., unipolar or bipolar). Bipolar pacing may be performed in the right ventricle using a bipolar transveous lead or in the left ventricle using a bipolar guidewire (e.g., Wattson Wire). Unipolar pacing may be performed in the right ventricle using a unipolar transveous lead and a grounding pad or in the left ventricle using a conventional guidewire and a grounding pad. The grounding pad may alternatively comprise a ground electrode attached to the access sheath or a ground electrode attached the chest.

In this example, the EPG 200 may be operated in four different modes: bipolar pacing for a balloon expandable valve mode; bipolar pacing for a self-expandable valve mode; unipolar pacing for a balloon-expandable valve mode; and unipolar pacing for a self-expandable valve mode. The desired mode may be selected by the cardiologist using user inputs on the EPG 200 or RCM 300, or at least partially automatically selected by detecting what type of lead 20 (unipolar or bipolar) is connected to the EPG 200. Alternatively, the RCM 300 may be configured for a single specific mode, wherein different models may be available for the desired mode. In either case, the mode of operation may be displayed by mode indicator 230.

The EPG 200 may, by way of example, not limitation, include other indicators such as pace rate 232, pairing status 234, heart rate (not shown), blood pressure (not shown), respiratory rate (not shown), other physiological indicators (not shown), and a display screen 236 for displaying a wide variety of selectable information such as instructions, procedural status, cardiac traces, physiologic information, etc. Pairing status indicator 234 may also be configured as a button, wherein short pressing (clicking) the button initiates pairing with RCM 300 and long pressing the button disables pairing and clears pairing memory. Additionally, the EPG 200 may have a display output connected to the lab monitor 30 to display a complete or partial mirror representation of the indicator information on the EPG 200 and/or RCM 300, in addition to static and/or cine views of the heart, intracardiac EGM, ECG, heart rate, respiratory rate and other physiologic or hemodynamic data. The EPG 200 may include different forms of indicators such as audio, visual and tactile indicators.

The housing 202 of the EPG 200 may contain (not visible) typical electrical components for a conventional EPG such as, for example, a power source (e.g., primary cell), a power control unit (e.g., for connection to an external power source), an output control module, an input control module, a pulse engine, a sensing module, a signal processing module, an indicator control module (e.g., audio, visual, tactile, display), etc., all of which may be configured to function according to the methods described herein. The EPG 200 may further include a communication module (e.g., two-way wireless) for communication with RCM 300, and a control module that includes a CPU with a memory unit for storing code and a processor for executing the code according to the methods described herein.

The RCM 300 may include a number of user inputs on the front of the housing 302, such as a primary button 306, an accessory button 308, an up button 310 and down button 312, each corresponding to the same buttons on EPG 200 with the same function. Each of the buttons may be back-lit to indicate status (lit=enabled/active; unlit=disabled/inactive). Note that the flowcharts may use "on" and "off" as shorthand for "active" and "inactive", respectfully. In addition, each button may distinguish between a short press (referred to herein as "click") and a long press (referred to herein as "press"), corresponding to different commands. The RCM 300 may also be equipped with tactile (e.g., haptic) and audio (tone) indicators to indicate status such as alerts or readiness. The housing 302 of the RCM 300 may contain (not visible) a power source (e.g., primary cell), a communication module (e.g., two-way wireless) for communication with EPG 200, and a control module, each of which may be configured to function according to the methods described herein. The RCM 300 may be wirelessly connected to the EPG 200 via a Bluetooth protocol, for example. The wireless connection between the EPG 200 and RCM 300 may provide for bidirectional exchange of information and commands.

The RCM 300 may have a form factor or shape as shown in FIG. 2 that is configured to rest on the operating table in the sterile field proximate the cardiologist operating the TAVR system, with optional attachment means for securement to sterile drapes or the like. Alternatively, the RCM 300 may be configured for attachment to the handle of the valve delivery device. For example, as shown in FIGS. 3A and 3B, the housing 302 may be configured to conform to and connect to the handle 70 of the valve delivery device. The underside of the housing 302 may be concave and include a mechanism for attachment to the handle of the valve delivery device such as, for example, a mechanical interlock or an adhesive strip. In FIG. 3A, a balloon-expandable inflation device 70 is shown, which acts as a handle that the cardiologist holds to facilitate delivery and deployment of the valve by balloon inflation. Alternatively, a self-expandable valve may be used with a corresponding handle for delivery and deployment of the valve by self-expansion. In either case, the RCM 300 may be disposed on the handle such that the cardiologist may simultaneously operate the RCM 300 and control the valve delivery system.

As mentioned elsewhere herein, if a conventional guidewire is used for lead 20 in a unipolar pacing configuration, a guidewire connector 50 may be used to connect the guidewire to the EPG 200 via cable 52. An example embodiment of a guidewire connector 50 is shown in perspective view and side view in FIGS. 4A and 4B, respectively. In this example embodiment, the guidewire connector 50 may comprise a clip with one or two sets of opposing arms 54. The arms 54 may be spring loaded and biased to a closed position to grip the guidewire 20 unless manually opened by the user. Each of the sets of arms 54 may include an upper arm 54A and a lower arm 54B, with corresponding conductive and opposing terminals 56A and 56B, respectively. The conductive terminals 56A and 56B may include one or more sharp edges configured to penetrate insulation on the guidewire 20 to achieve an electrical connection to the metal portion thereof. Additionally, the conductive terminals 56A and 56B may include an irregular geometry for gripping the guidewire 20. The irregular geometry may comprise, for example, a convex surface or protrusion and a corresponding concave surface or recess, which may be aligned or offset to enhance grip.

The system 100 may be operated in four different stages, for example. The stages may be executed based on inputs from the RCM 300 and/or the EPG 200. Execution of these stages may be assisted by automation, for example by instructions contained in the code stored in the memory of the CPU and executed by the processor as described previously. Such instructions and the associated methods may be explained by the various stages schematically illustrated in FIG. 5. Such stages may be executed alone or in combination, and the sequence of execution may be as shown, by way of example, not limitation.

As seen in FIG. 5, which schematically illustrates an overview of the operational stages, operation of the system 100 may start 590 with a continuity test 600. Basically, the continuity test (CT) 600 determines 602 if there is a non-intermittent electrical connection between the EPG 200 and the lead 20, including the guidewire connector 50 and cable 52. CT 600 may be initiated automatically upon connecting EPG 200 and lead 20 (e.g., based on a sensed connection, a connection based trigger, upon initiating EPG 200, or the like) or may be selectively initiated in response to user input. If no continuity is found, then the operator may check and fix 604 such connections as appropriate, after which the continuity test 600 may be repeated. Note that the continuity test 600 may be periodically repeated throughout the operation of the system 100, except during portions where it may interfere with the stage of operation in progress, such as a portion of the capture check. Continuity may be determined by applying an extremely small current to the lead, in accordance with ISO60601-1, and measuring the resulting voltage. Once continuity is found, the operation may move to the next stage.

The next stage may be a capture check (CC) 700 which determines 702 if 1:1 capture can be established, i.e., if the HR corresponds 1:1 with PPR. Lack of 1:1 capture may be due to the lead 20 not being in adequate contact with (pace-able) intracardiac tissue. Lack of 1:1 capture may also occur due to premature ventricular contraction (PVC), wherein the heart contracts before responding to a pacing signal. Such lack of 1:1 capture may be adjudicated and adjusted 704, e.g., by the cardiologist. Depending on the cause, such adjustments may include, for example, changing the position of the lead 20 to establish better contact with intracardiac tissue, ramping the PPR up and/or down, etc. Once adjudicated and adjusted 704, the capture check 700 may be repeated, and once 1:1 capture is confirmed 702, the operation may move to the next stage.

The next stage may be rapid pacing (RP) 800 which determines 802 if the pacing conditions (e.g., PPR) and heart status (e.g., HR) are appropriate for valve deployment. Generally speaking, at a sufficiently high paced HR, the stroke volume goes down to reduce the pressure gradient across the native valve annulus to mitigate valve embolization during deployment of a balloon expandable valve or to increase stability during deployment of a self-expanding valve. During RP 800, the PPR of a pacing output maybe modified (e.g., increased or decreased) in response to receiving a user readiness input. According to an embodiment, the indicator may be triggered based on when the PPR and/or HR meet(s) a provided or selected setting (e.g., provided by a healthcare provider). The indicator may be triggered when the PPR and/or HR meet(s) the user provided or selected setting. If it is determined 802 that the conditions are satisfied (e.g., if the PPR and/or HR meet(s) a setting), the valve may be deployed 1000 by the cardiologist. However, if it is determined 802 that the conditions are not satisfied, the cause may be adjudicated and adjusted 804, e.g., by the cardiologist, after which the rapid pacing stage 800 may be repeated. An example of where conditions are not satisfied is lack of 1:1 capture due to heart block, wherein the PPR is faster than the heart is able to respond. In such a case, the PPR may be greater than the HR, for example 2:1. Alternatively, failure to achieve the appropriate conditions may require a repeat of CT 600, CC 700, and/or back-up pacing (BP) 900.

Once the valve is deployed 1000, the operation may enter a BP stage 900. Generally, the BP stage 900 may be used to return the heart 10 to its intrinsic HR from the elevated PPR used for valve deployment. This may be accomplished by reducing the PPR until HR>PPR wherein the pace signal is inhibited in VVI mode (pace ventricle, sense ventricle, inhibit if intrinsic). VVI is standard pacing nomenclature in which the first letter is the chamber paced, the second letter is the chamber sensed and the third letter is the response to a sensed beat. In this case, the ventricle is paced, the ventricle is also sensed, and if a beat is sensed it inhibits the next pacing spike. This helps prevent the "R on T" phenomenon in which a pacer activates in the repolarization phase of the heart beat which can cause ventricular fibrillation and sudden death.

FIG. 6, which is a schematic flow diagram, provides more detail on the CC stage 700, by way of example, not limitation. The CC stage 700 starts 696 with the cardiologist positioning 698 the lead 20 in the desired position for pacing. A confirmatory CT may be performed, wherein continuity is determined 602. If continuity is not found 602, then the connections of the lead 20 to the EPG 200 may be checked and fixed 604, and the lead position reestablished 698. If continuity is found, the EGM signal may be sensed 708. If EGM is not detected, the lead position may be repositioned 697 to receive a better signal. If EGM is detected, the EPG 200 may begin ramping up the pacing signal 710, wherein the PPR may begin empirically around 80 to 120 pulses per minute (i.e., beats per minute (BPM)), ramping up at a rate of 5 to 15 pulses per minute every 1 to 5 seconds, for example, wherein the PPR is not to exceed around 130 to 160 pulses per minute by the automatic algorithm. Alternatively, the initial PPR may begin at a rate calculated by measuring HR and adding 50 BPM, for example. If needed, the operator may manually raise the HR up to a maximum of 200 pulses per minute using 310. By way of example, not necessarily limitation, the pacing signal may be set to a pulse amplitude of approximately 1 to approximately 7 mA, and a pulse width of approximately 80 to approximately 140 ms, and preferably a pulse amplitude of approximately 7 mA and a pulse width of approximately 140 ms, in VVI mode. While ramping up the PPR, a 1:1 capture check may be confirmed 702. If it is determined 702 that 1:1 capture has not been established, it may then be determined 714 if the lead is in contact with pace-able tissue. If the lead is not in contact with pace-able tissue, the lead may be repositioned 697 and the loop may repeat. If it is determined that the lead is in contact with pace-able tissue, the pace rate may be ramped up 710 until 1:1 capture is established. When it is determined 702 that 1:1 capture has been initially established, capture may be confirmed over at least one respiratory cycle 712 (e.g., around 6 to 10 seconds) to be certain capture can be maintained independent of heart movement due to respiration. Once capture is confirmed for at least one respiratory cycle, the PPR may be ramped down to approximately 50 BPM, for example, a rate of approximately 5 to approximately 15 BPM for approximately 5 to approximately 15 seconds, for example, wherein the PPR does not fall below around 30 to 50 pulses per minute. The PPR may be ramped down until it is determined 904 that pacing is inhibited (i.e., until HR>PPR meaning intrinsic pacing takes over). The steps of ramping down PPR 902 and determining if pacing is inhibited 904 are similar to the basic steps of back-up pacing 900. Once capture check 700 is complete, the operation may move to the next stage (e.g., RP stage 800).

Pacing parameters for CC may be different (lower in amplitude/pulse width) than the pacing parameters used during RP to provide safety margin. I.e., finding the best location for pace-able tissue at a lower pace amplitude will be a smaller zone. Should the lead move a little during RP, the higher pacing amplitude will help overcome the change and ensure capture is maintained.

FIG. 7, which is a schematic flow diagram, provides more detail on the RP stage 800, by way of example, not limitation. The RP stage 800 starts 796 with the cardiologist positioning 798 the valve in the desired position prior to deployment, e.g., proximate the valve annulus. The EPG 200 may send a pacing signal, ramping from around 140 to around 200 pulses per minute above the sensed HR, ramping up at a rate of approximately 10 to approximately 20 pulses per minute every approximately 0.5 to approximately 2 seconds, for example. By way of example, not necessarily limitation, the pacing signal may be set to a pulse amplitude of approximately 10 to approximately 25 mA, and a pulse width of approximately 80 to approximately 140 ms, or preferably a pulse amplitude of approximately 25 mA and a pulse width of approximately 140 ms, in VVI mode. While ramping up the PPR, 1:1 capture may be confirmed 702, and if 1:1 capture is lost at any time before valve deployment 1000, the pacing signal may be ramped down 902 until it is determined 904 that pacing is inhibited. While ramping up the PPR, heart block may also occur if the PPR exceeds the capability of the heart. Should that occur, PPR may be reduced gradually until capture is reestablished. If 1:1 capture is maintained, the PPR may be ramped until reaching a desired threshold X corresponding a condition where 1:1 capture is possible and is still suitable for valve deployment, such as a PPR of around 160 to around 180 beats per minute, or preferably at least 160 beats per minute with adequate hypotension as determined by the cardiologist, for example. Once it is determined 812 that the PPR is at the desired threshold, the valve may be deployed 1000 by the cardiologist. After successful valve deployment 1000, the pacing signal may be dropped or ramped down 902 (e.g., to VVI 80 BPM) until it is determined 904 that pacing is inhibited, after which the operation can move to the next stage (e.g., BP stage 900).

FIGS. 8-13 show detailed steps for using the system 100 according to example embodiments. For purposes of explanation, not necessarily limitation, the steps are organized according to the operational stages mentioned above. Throughout FIGS. 8-13, boxes shown in dashed lines are generally steps that may performed by the cardiologist, and boxes shown in solid lines are generally steps that may be at least partially performed by executable code. The steps and processes are illustrated in flow diagrams, wherein the flow diagrams between pages are connected by common nodes (small black circles with letters).

Figure 8:
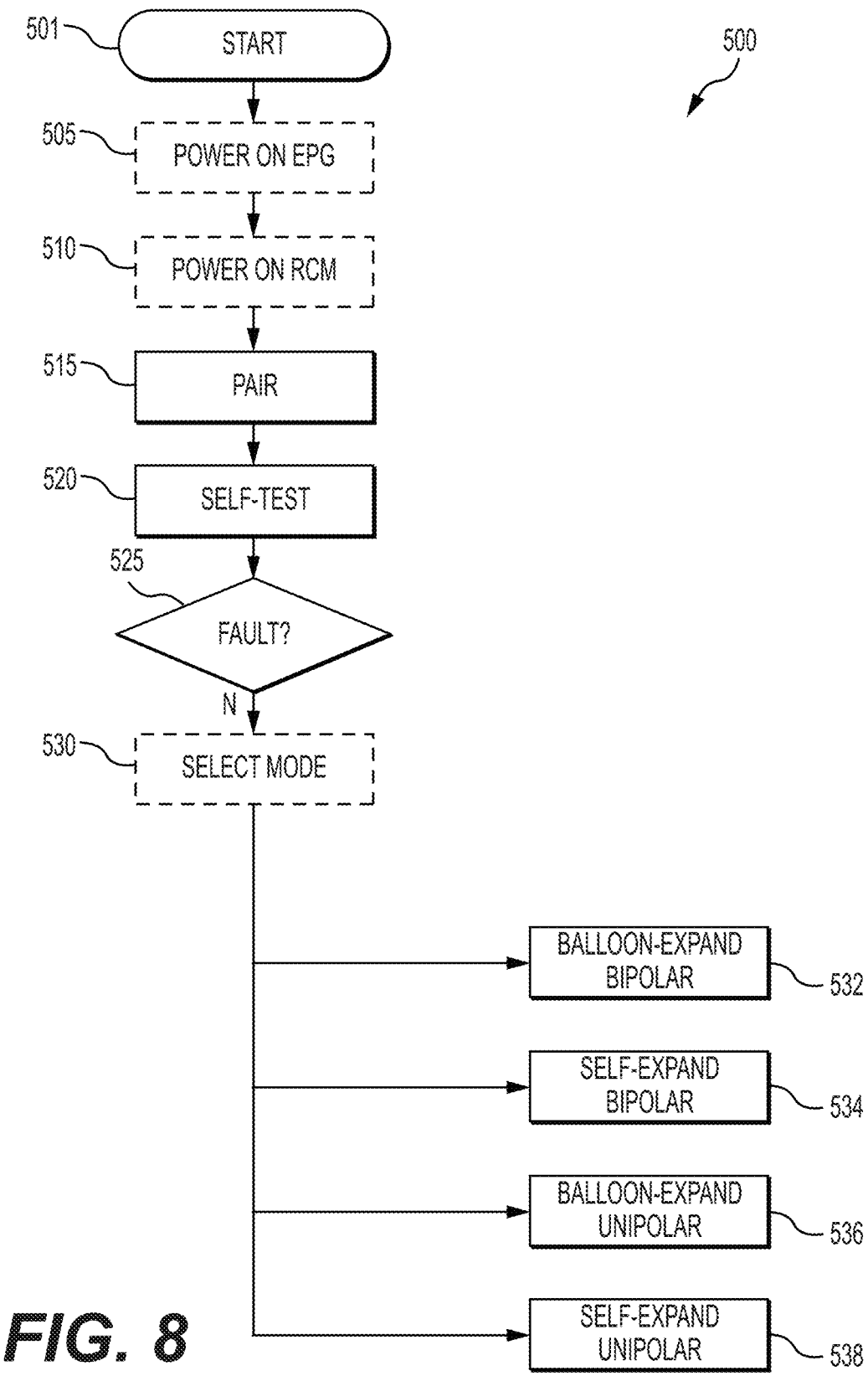

FIG. 8 is a flow chart illustrating a start-up process 500 for using the EPG 200 and RCM 300, according to an example embodiment. To start 501, the EPG 200 may be powered on 505 by pressing the power button on the EPG 200. The RCM 300 may then be powered on 510 by actuating an on-off switch on the back of the RCM (not visible) or by removal of an insulated packing strip, for example, covering a battery terminal. The EPG 200 and the RCM 300 may then be paired 515 by Bluetooth, for example, to provide bidirectional wireless communication. The EPG 200 may then execute a self-test 520 to check for faults in pairing, communication and other electrical faults. If faults are found, pairing may be repeated. If no faults are found, the desired mode may be selected 530. As described previously, the four modes may include: bipolar pacing for a balloon expandable valve mode 532; bipolar pacing for a self-expandable valve mode 534; unipolar pacing for a balloon-expandable valve mode 536; and unipolar pacing for a self-expandable valve mode 538. Generally speaking, the flow charts shown in FIGS. 8-13 are with reference to bipolar balloon expandable mode 532, but the same processes may be used for the other modes 534, 536 and 538 with modest modifications described hereinafter.

Figure 9:
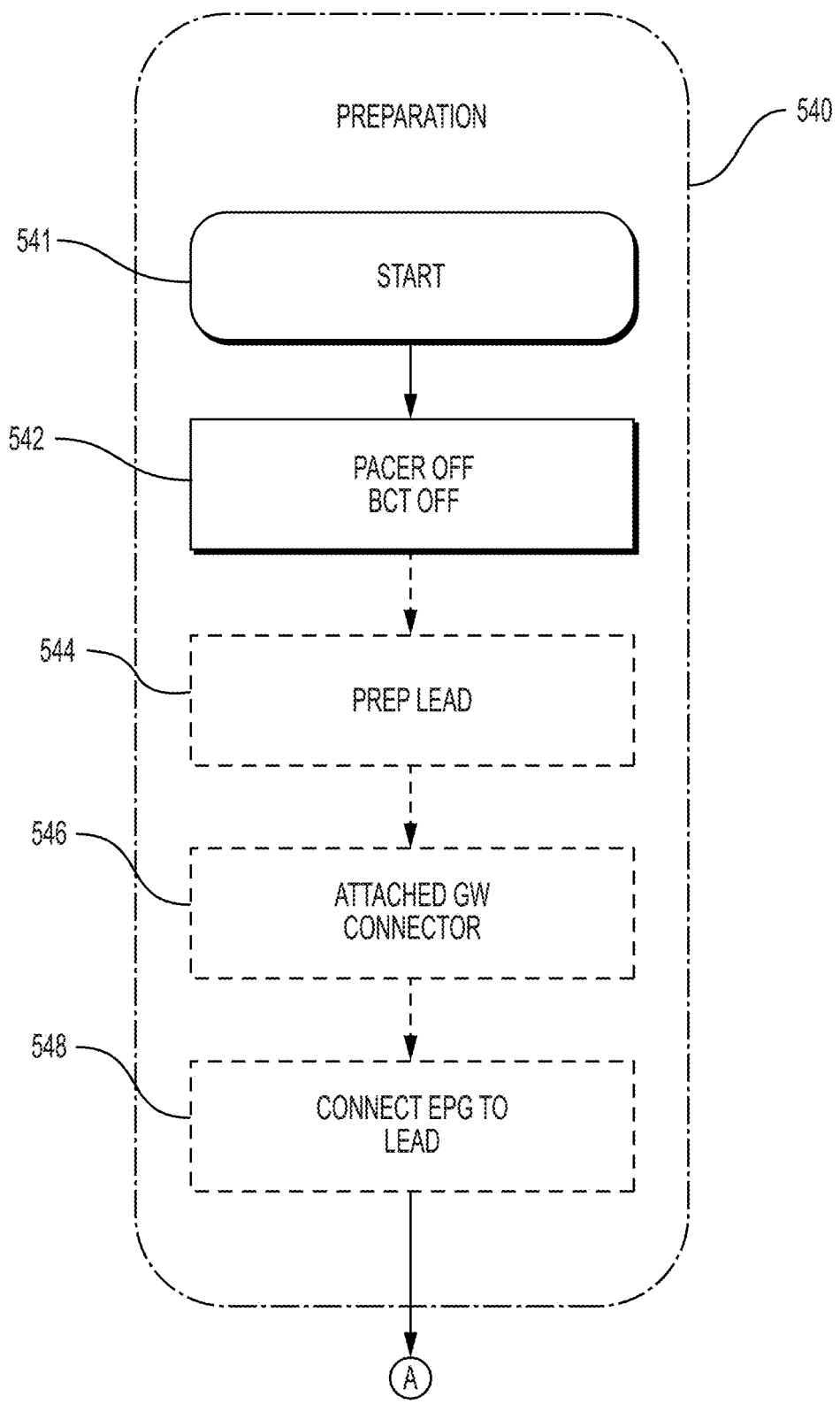

FIG. 9 is a flow chart illustrating a preparation process 540 according to an example embodiment. To start 541, the pacer (in the EPG 200) and the background continuity test (described hereinafter) may be set to off. The scrub nurse may prepare 544 the lead 20 according to standard practice, plug a connector cable into the EPG 200 and attach 546 the guidewire connector 50 to the lead 20. The cable 52 may be connected 548 to the EPG 200, and if operating in unipolar mode 536, 538, the grounding pad 60 may be connected to the EPG 200 via cable 62. The process may then proceed to the CT process 600 via node A.

Figure 10A:
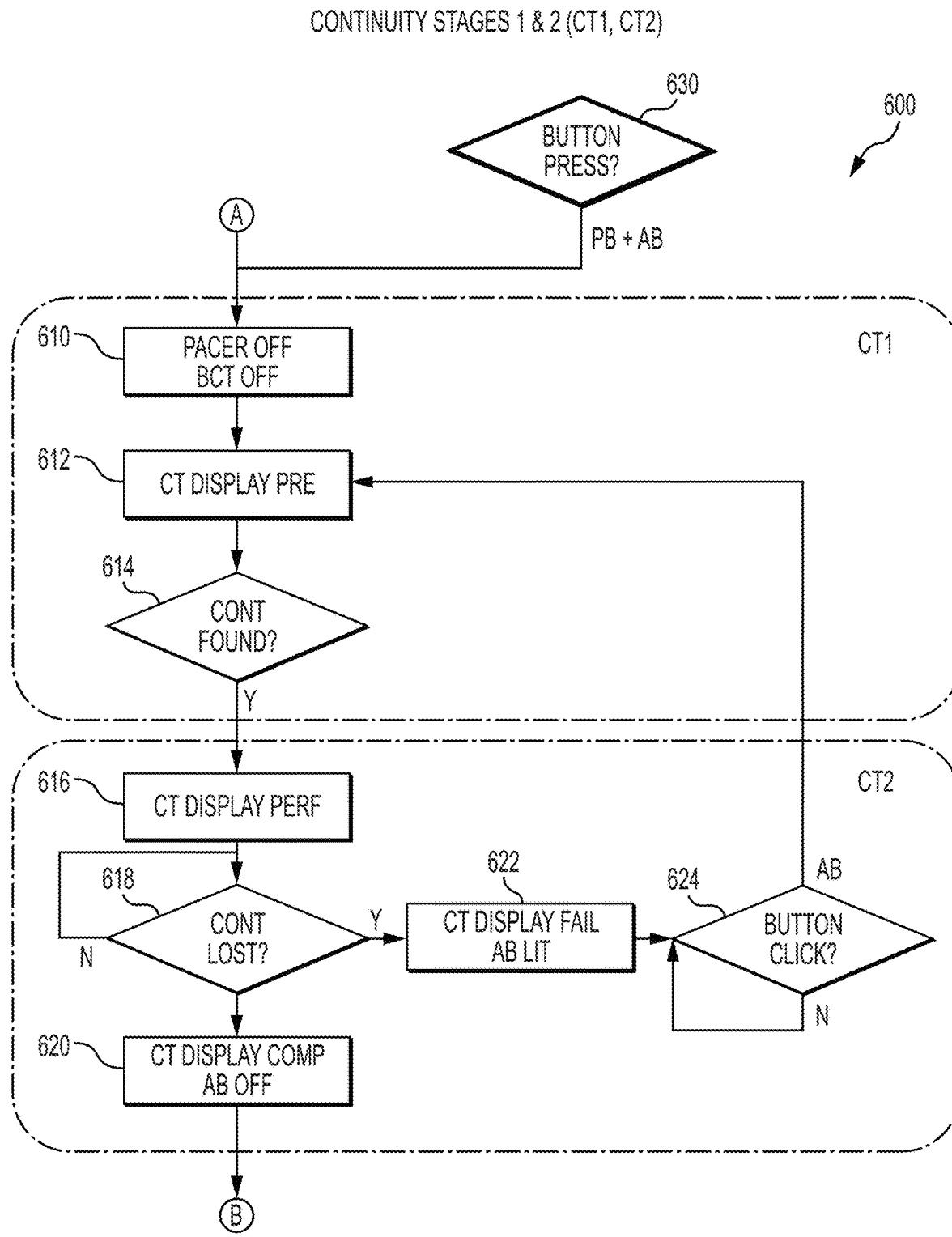

FIG. 10A is a flow chart illustrating a CT process 600 according to an example embodiment. The CT 600 may be broken down into two stages: continuity test 1 (CT1) wherein the process waits for the user to be ready before verifying lead continuity; and continuity test 2 (CT2) wherein the continuity of the lead is verified over a period of time (e.g., several seconds). In CT1, the pacer and background continuity test are initially set to off 610 and the continuity test indicator 220 displays pretest status 612. Continuity is monitored and once found 614 (suggesting the lead 20 is connected to the EPG 200 and the lead 20 is in a saline soak) the process may proceed to CT2 to confirm continuity. In CT2, the continuity test indicator 220 may display performing status 616. Continuity is monitored for a period of time and if it is determined 618 the continuity is not lost after the period of time expires (timeout), the continuity test indicator 220 may display complete status 620 and the accessory buttons 208 and 308 may be disabled (unlit). The process may then proceed to CC 700 via node B.

However, if it is determined 618 that continuity has been lost, the continuity test indicator 220 may display failed status, and the accessory buttons 208 and 308 may be enabled and lit 622. The process may then wait for the accessory button 208 or 308 to be clicked to go to the next step. Once it is determined 624 that the accessory button 208 or 308 has been clicked, the process may return to CT1 to repeat the continuity test 600. At any time during the operational stages, if it is determined 630 that the primary button 206/306 and the accessory button 208/308 have been long pressed at the same time, CT1 may be initiated directly at step 610.

Figure 10B:
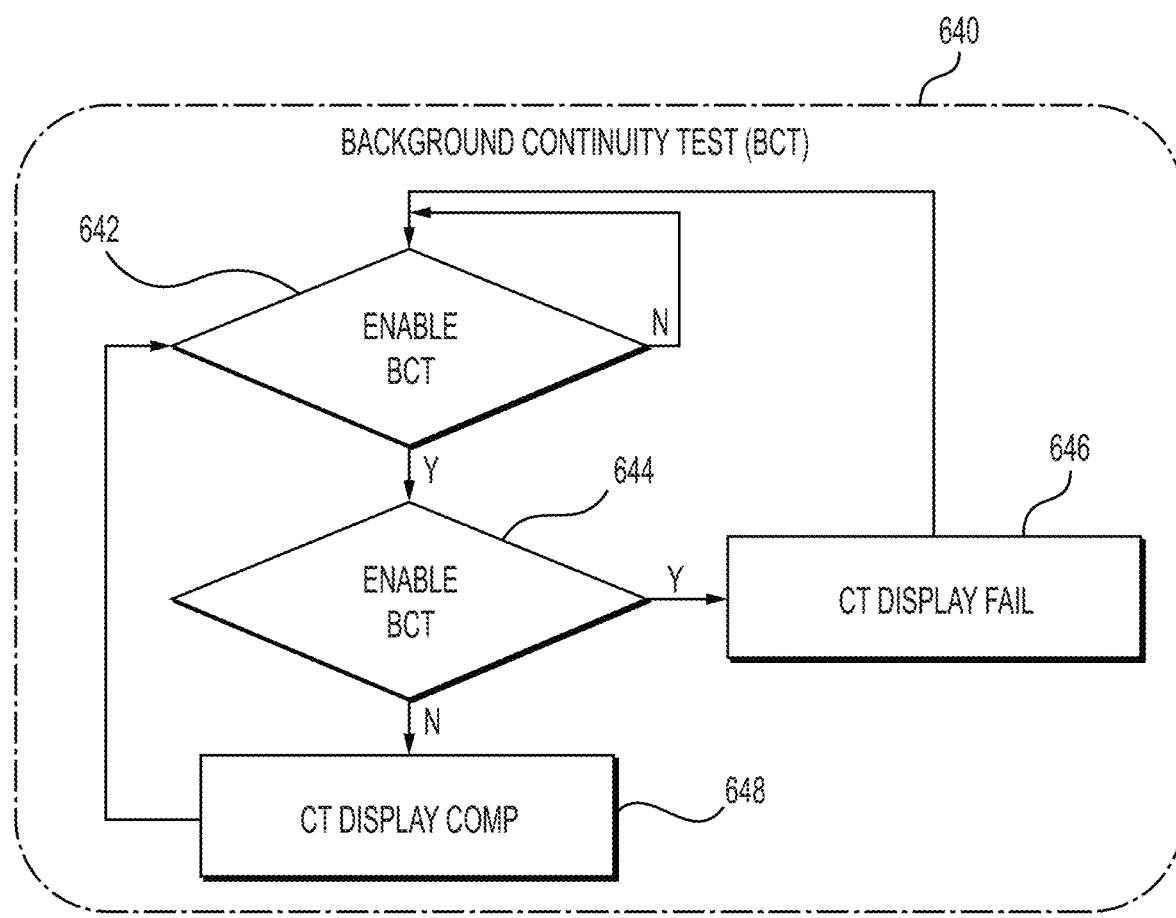

FIG. 10B is a flow chart illustrating a back ground continuity test (BCT) process 640 according to an example embodiment. The BCT 640 may run continuously in the background unless specifically disabled. For example, in some instances, other processes may have an embedded continuity test, the outcome of which may be unique to the process being executed. If it is determined 642 that the BCT is enabled, continuity is monitored and if it is determined 644 that continuity has been lost, the continuity test indicator 220 may display failed status 646. If it is determined 644 that continuity has not been lost, the continuity test indicator 220 may (continue to) display complete status 648.

FIGS. 11A-11D are flow charts illustrating a CC process 700 according to an example embodiment. The CC 700 process may be broken down into four stages: capture check stage 1 (CC1) wherein the process waits until continuity is confirmed and EGM is detected; capture check stage 2 (CC2) which automatically determines the appropriate PPR for capture check and automatically ramps PPR; capture check stage 3 (CC3) which automatically verifies capture over at least one respiratory cycle; and capture check stage 4 (CC4) which provides, in the alternative, allows for manually ramping of PPR with user input.

Figure 11A:
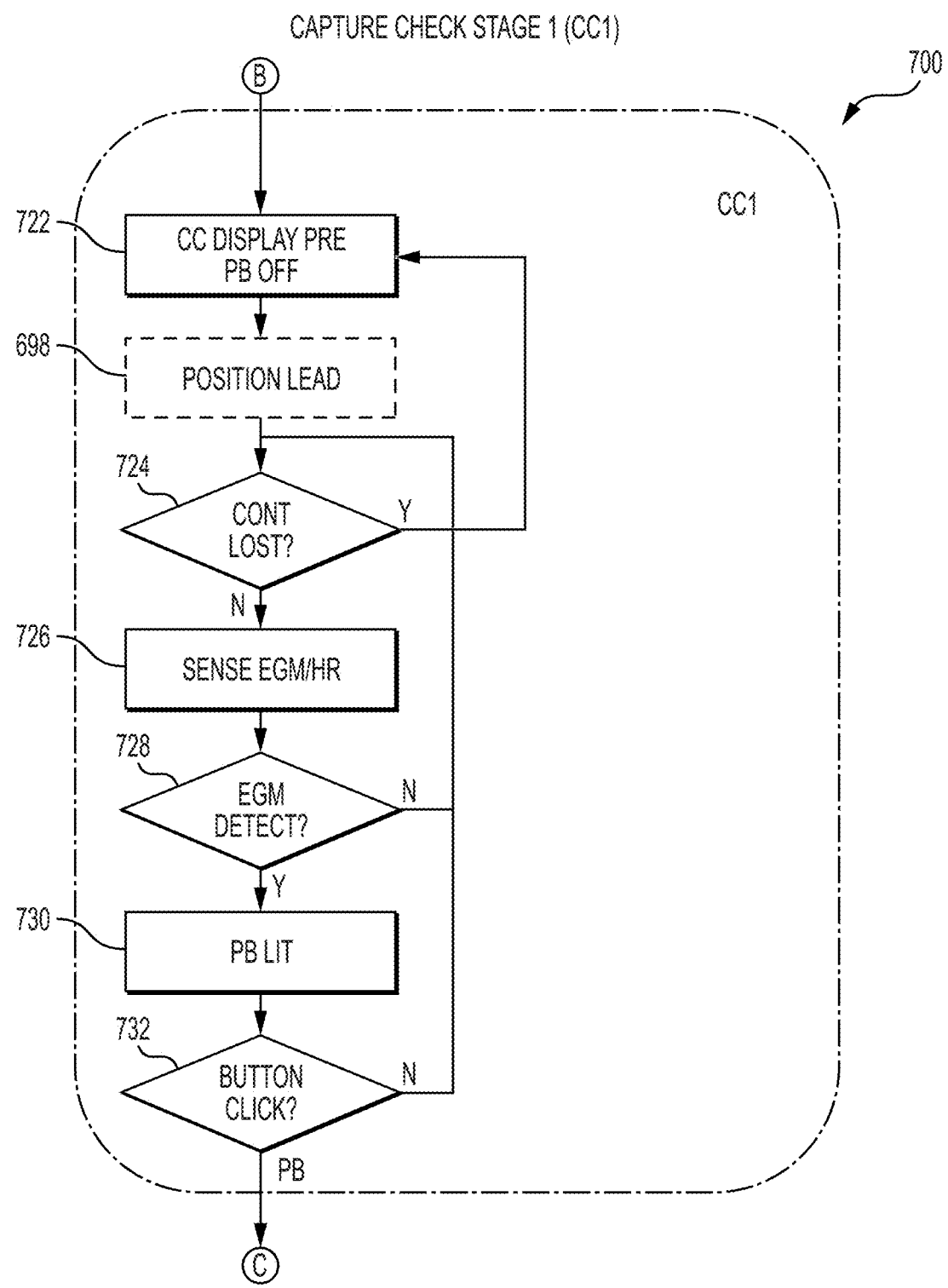

With reference to FIG. 11A, CC1 may begin with the capture check indicator 222 displaying pre-capture check status 722 and the primary buttons 206 and 306 disabled (unlit). The cardiologist may then position 698 the lead 20 in the desired position for pacing. A confirmatory continuity test may be performed and if it is determined 724 that continuity has been lost, the process may return to step 722. If it is determined 724 that continuity has not been lost, EGM may be sensed 726, from which HR may be derived. If it is determined 228 that EGM is not detected or not of sufficient amplitude, the process may return to step 724, and the cardiologist may consider repositioning the lead 20 to obtain a better signal. If it is determined 728 that EMG is detected, the primary buttons 206 and 306 may be enabled and lit 730, and if it is determined 732 that the primary button 206 or 306 has been clicked, the process may proceed to CC2 via node C.

Figure 11B:
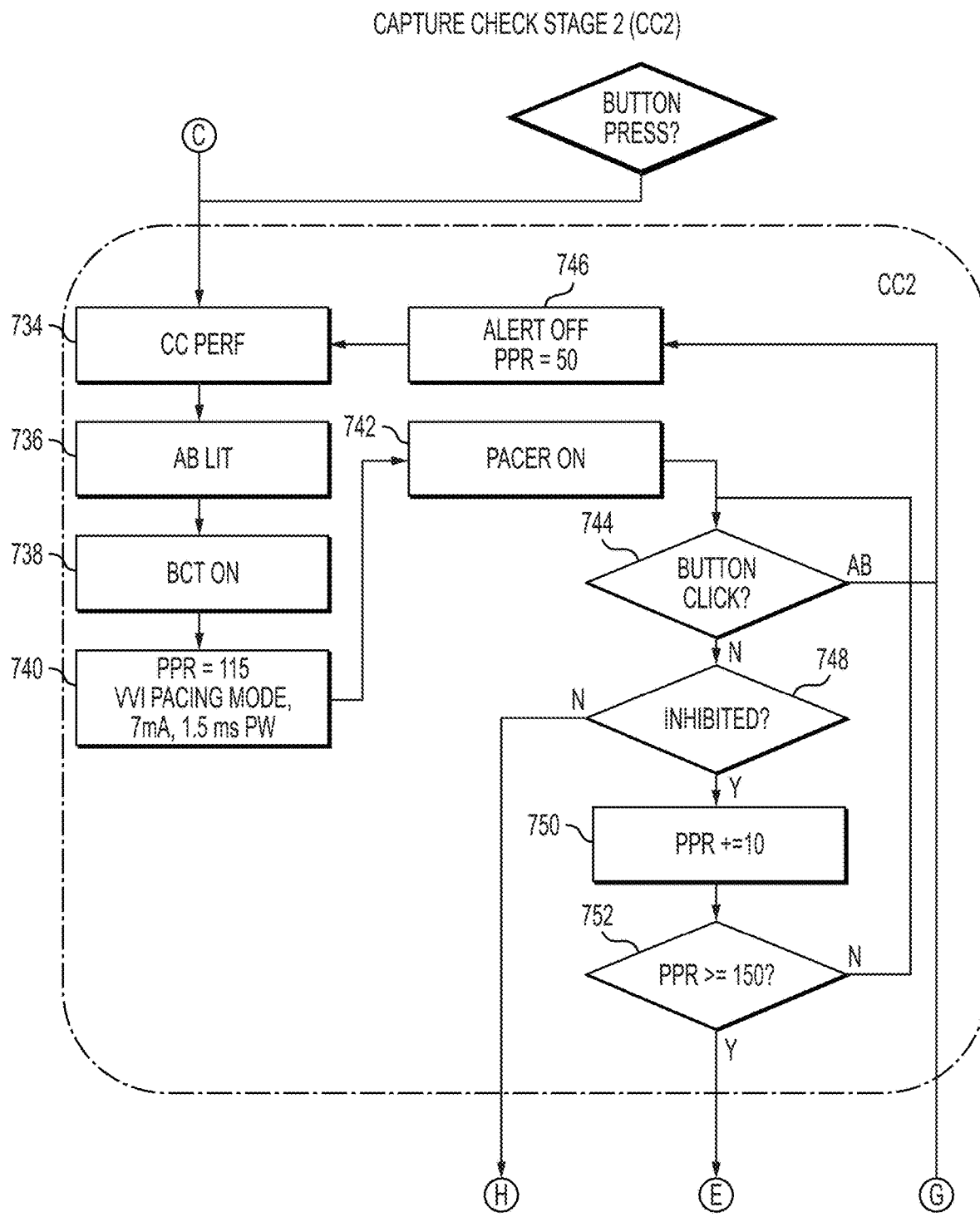

With reference to FIG. 11B, CC2 may begin with the capture check indicator 222 displaying perform status 722. At any time during the operational stages, if it is determined 790 that the accessory button 208 or 308 has been long pressed, CC2 may be initiated directly. The accessory buttons 208 and 308 may then be lit 736 and the BCT may be turned on 738. The PPR may be set approximately 740 to approximately 115 BPM in VVI pacing mode, with an amplitude of approximately 7 mA and a pulse width of approximately 1.5 ms, for example. The pacer may be turned on 742 and the process may then execute a loop where the PPR is automatically ramped up to approximately 150 BPM. This loop starts with determining 744 if the accessory button 208 or 308 has been clicked, and if so, exits the loop, turns off the alert 746, sets the PPR to approximately 50 BPM and returns to step 734 to restart CC2. If the accessory button 208 or 308 has not been clicked, a determination 748 is made if pacing has been inhibited (i.e., HR>PPR). If pacing has not been inhibited (i.e., PPR>HR, suggesting initial capture), the process exits the loop and enters CC3 (capture confirmation) via node H.

However, if pacing has been inhibited (i.e., HR>PPR), the PPR may be increased by 10 BPM, for example, at step 750. A determination 752 may then be made if the PPR is greater than approximately 150 BPM, for example. If it is determined 752 that the PPR is less than approximately 150 BPM, the loop repeats at step 744 to continue automatic ramping. If it is determined 752 that the PPR is greater than or equal to approximately 150 BPM, the process exits the loop and enters CC4 (manual ramping) via node E. This step may be described as a way to avoid continued automatic ramping when the PPR is above approximately 150 BPM with inhibition, suggesting the HR>150 without initial capture, which may be a safety concern for the patient and warrants manual adjustment of PPR in CC4.

Figure 11C:
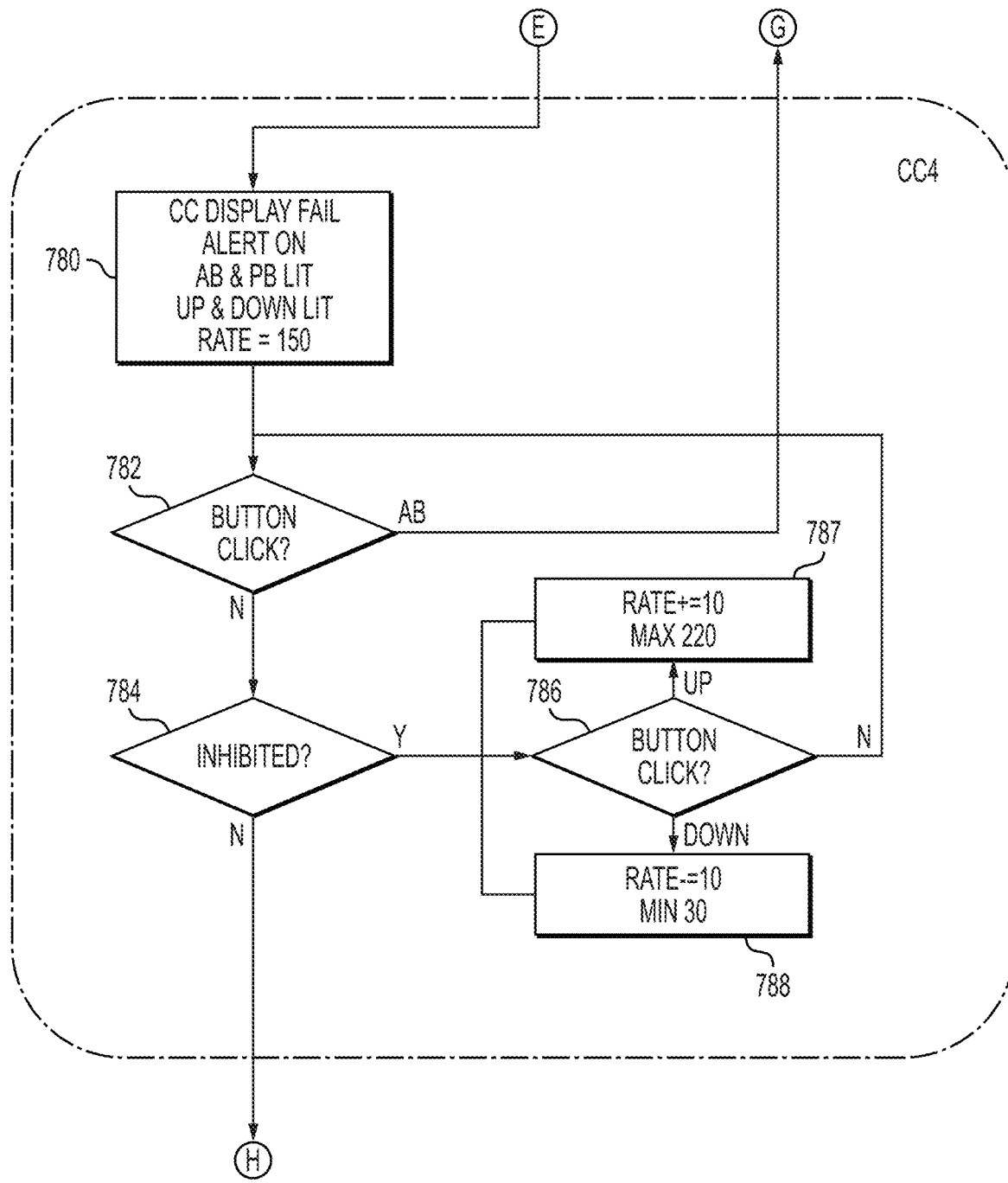

With reference to FIG. 11C, manual ramping stage CC4, if needed, may begin at 780 with the capture check indicator 222 displaying failed status, alert on, the primary buttons 206 and 306, the ancillary buttons 208 and 308, the up 210, 310 and down 212, 312 buttons enabled and lit, and the PPR set to approximately 150 BPM. A determination 782 is made if the ancillary button 208 or 308 has been clicked. If so, the process returns to step 746 via node G to reattempt automatic ramp in stage CC2. If not, a determination 784 is made if pacing is inhibited. If pacing is not inhibited, the process may proceed directly to capture verification in stage CC3 via node H. If pacing is inhibited, a determination is made if the up 210/310 button or the down 212/312 button is clicked. Clicking 787 the up button 210 or 310 may increase the PPR by approximately 10 BPM, for example, up to a maximum of approximately 200 BPM, for example. Clicking 788 the down button 212 or 312 may decrease the PPR by 10 BPM, for example, down to a minimum of 30 BPM, for example. This allows the cardiologist to manually increase or decrease the PPR in an effort to troubleshoot lack of capture. If neither button is clicked or when button clicking has stopped, the loop may be repeated by returning to step 782 until pacing is no longer inhibited, and the process may then proceed to capture verification in stage CC3 via node H.

Figure 11D:
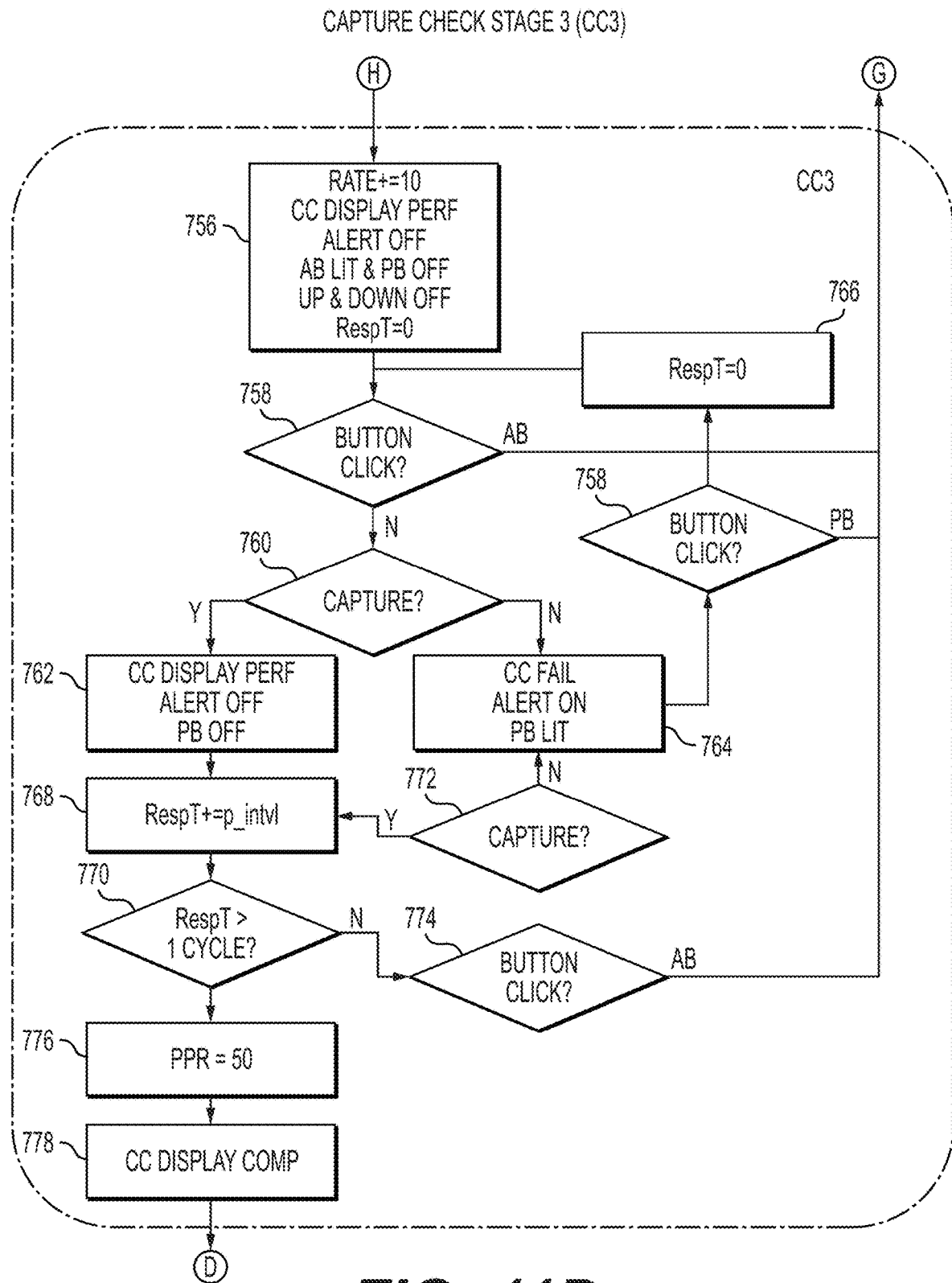

With reference to FIG. 11D, CC3 (capture verification) may begin at step 756 with the capture check indicator 222 displaying perform status, alerts off (if any), the accessory buttons 208 and 308 enabled and lit, the primary buttons 206 and 306 disabled and unlit, the up 210, 310 and down 212, 312 buttons disabled and unlit, the respiratory time (RespT) set to zero, and the PPR being increased by approximately 10 BPM, for example. The process may then enter a loop to automatically confirm capture over a period of time corresponding to at least one respiratory cycle. This loop may start by determining 758 if the accessory button 208 or 308 has been clicked, and if so, exiting the loop to return to CC2 via node G. Otherwise, a determination 760 is made if 1:1 capture has been obtained. If 1:1 capture is not present, the capture check indicator 222 displays failed status, the primary buttons 206 and 306 are enabled and lit, and an alert is turned on at step 764. The process then waits to determine 765 if the primary button 206 or 306 has been clicked, and if so, the loop restarts at step 758 after the respiratory time has been reset to zero at step 766. If capture is present, the loop continues at step 762 with the capture check indicator 222 displaying or continuing to display perform status, the primary buttons 206 and 306 off and alerts off (if any). The respiratory time may then be incremented up an interval (p_intvl) corresponding to 1 second, for example, at step 768. A determination 770 is made if the respiratory time has reached the equivalent of 1 respiratory cycle (e.g., approximately 8 seconds), and if not, the process repeats by checking capture 772 and incrementing the respiratory time 768. If the accessory button 208 or 308 is clicked 774 while the process is repeating, the loop is exited to return to CC2 via node G. Once capture has been confirmed for a period of time equivalent to at least one respiratory cycle, the PPR may be set to 50 BPM at step 776, the capture check indicator 222 may display complete status at step 778, and the process may proceed to the RP process via node D.

Figure 12A:
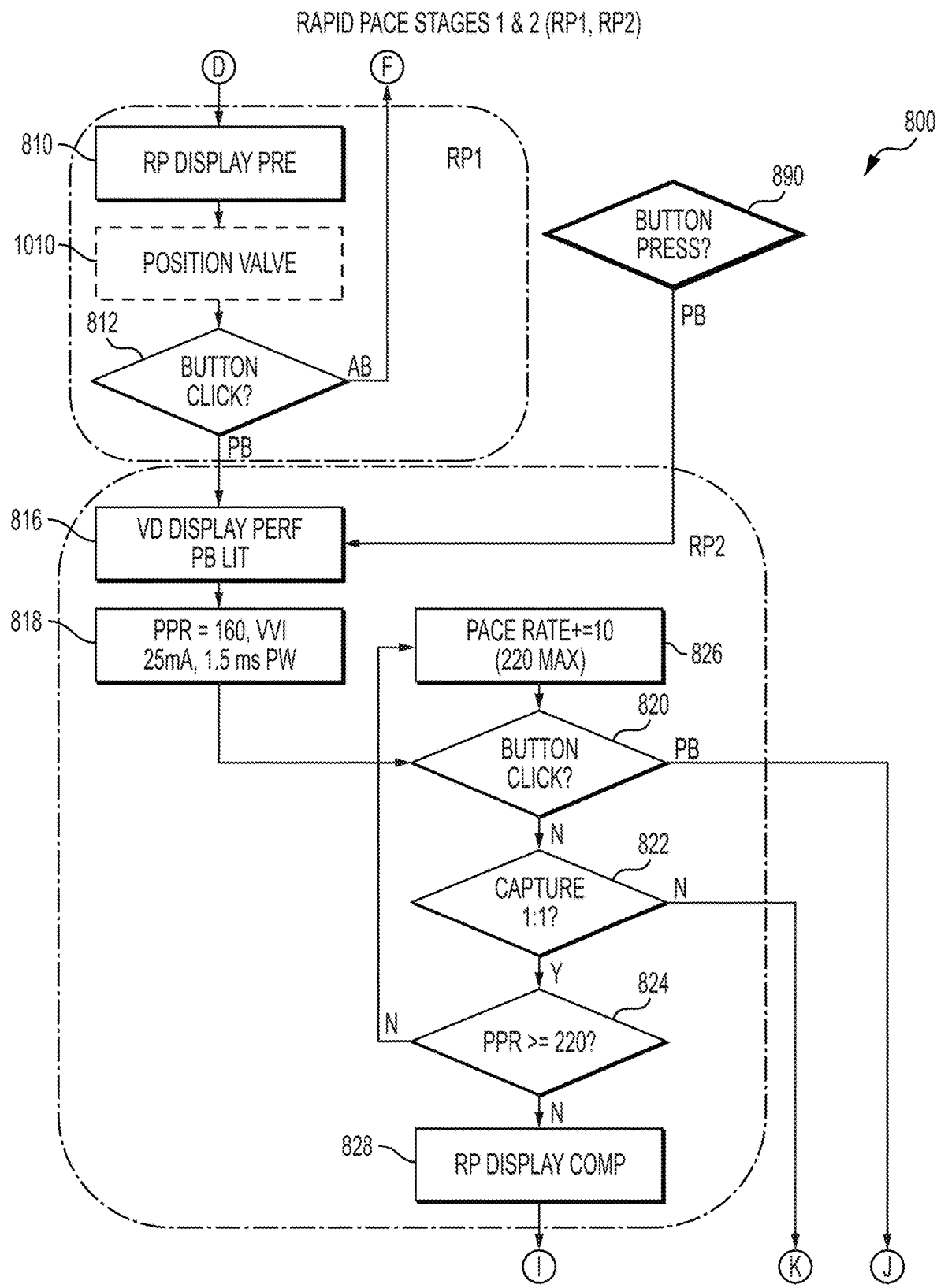
Figure 12B:
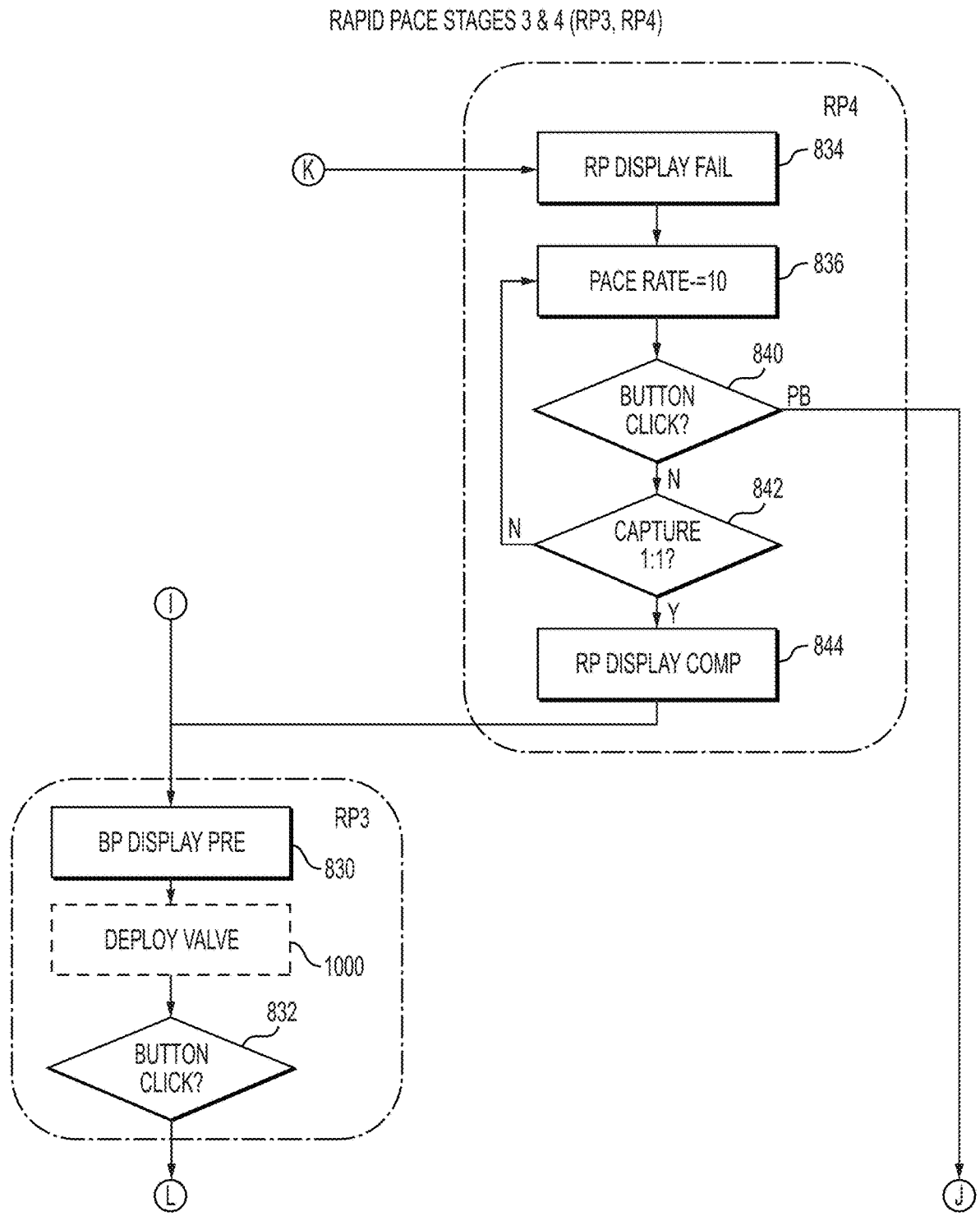

FIGS. 12A and 12B are flow charts illustrating a RP process 800 according to an example embodiment. The RP process 800 may be broken down into four stages: rapid pacing stage 1 (RP1) wherein the process waits until the cardiologist is ready; rapid pacing stage 2 (RP2) which automatically ramps up PPR to a suitable level for valve deployment; rapid pacing stage 3 (RP3) wherein the cardiologist deploys the valve; and rapid pacing stage 4 (RP4) which automatically ramps down PPR in an attempt to regain capture if lost in RP2.

With reference to FIG. 12A, RP1 may begin at step 810 with the valve deployment indicator 224 displaying pre-deployment status. The cardiologist may then get the valve into position 1010 for deployment. A determination 812 may be made as to whether either the primary button 206/306 or the accessory button 208/308 has been clicked. If it is determined 812 that the primary button 206 or 306 has been clicked, indicating the cardiologist is ready to continue, the process may proceed to RP2. If it is determined 812 that the accessory button 208 or 308 has been clicked, indicating the cardiologist wants to repeat capture check, the process may return to CC2 via node F.

With continued reference to FIG. 12A, RP2 may begin at step 816 with the valve deployment indicator 224 displaying perform status, and the accessory buttons 208 and 308 enabled and lit. At any time during the operational stages, if it is determined 890 that the primary button 206 or 306 has been long pressed, RP2 may be initiated directly at step 816. At step 818, the PPR may then may then be set to 160 BPM in VVI mode with an amplitude of approximately 25 mA and a pulse width of approximately 1.5 ms, for example. The process may then enter a loop whereby the PPR is automatically increased in increments of approximately 10 BPM, for example, until the PPR is equal to or greater than approximately 200 BPM, for example. Each cycle through the loop offers the cardiologist the opportunity to exit to back-up pacing. The loop may begin with a determination 820 as to whether the primary button 206 or 306 has been clicked. If the primary button 206 or 306 has been clicked, the BP process 900 may be initiated directly at via node J. If the primary button 206 or 306 has not been clicked, a determination may be made regarding capture. If 1:1 capture is not present, then the process may proceed to RP4 via node K. If 1:1 capture is present, a determination 824 may be made as to whether the PPR has reached approximately 200 BPM or more. If the PPR is less than approximately 200 BPM, the PPR may be increased by 10 BPM, for example, at step 826, and the loop repeats. If the PPR is equal to or greater than approximately 200 BPM, the valve deployment indicator 224 may display complete status at step 828 and the process may proceed to RP3 via node I.

With reference to FIG. 12B, RP3 may begin at step 830 with the back-up pacing indicator 226 displaying pre-back-up pacing status. With the valve deployment indicator 224 already displaying complete status, the cardiologist may then deploy the valve at step 1000. A determination 832 may then be made as to whether the primary button 206 or 306 has been clicked, indicating the valve deployment has been successful or at least attempted, and the process may proceed to BP via node L.

With continued reference to FIG. 12B, RP4 may be entered in an attempt to regain capture lost in RP2 by reducing PPR, starting at step 834 with the valve deployment indicator 224 displaying failed status. A loop may then begin to automatically ramp down the PPR, check to see if capture has been regained, and offer the cardiologist an opportunity to exit the loop to enter back-up pacing. The loop may be triggered automatically or may be triggered in response to user input. The loop may begin by reducing the PPR by increments of 10 BPM, for example, at step 836. A determination 840 may then be made to see if the cardiologist has clicked the primary button 206 or 306. If the primary button 206 or 306 has been clicked, the loop may be exited to BP via node J. If the primary button 206 or 306 has not been clicked, the loop continues by determining 842 if capture has been regained. If capture has not been regained, the loop repeats ramping PPR down at step 836. If capture has been regained, the valve deployment indicator 224 changes to complete status, and the process may continue to RP3 for valve deployment.

Figure 13:
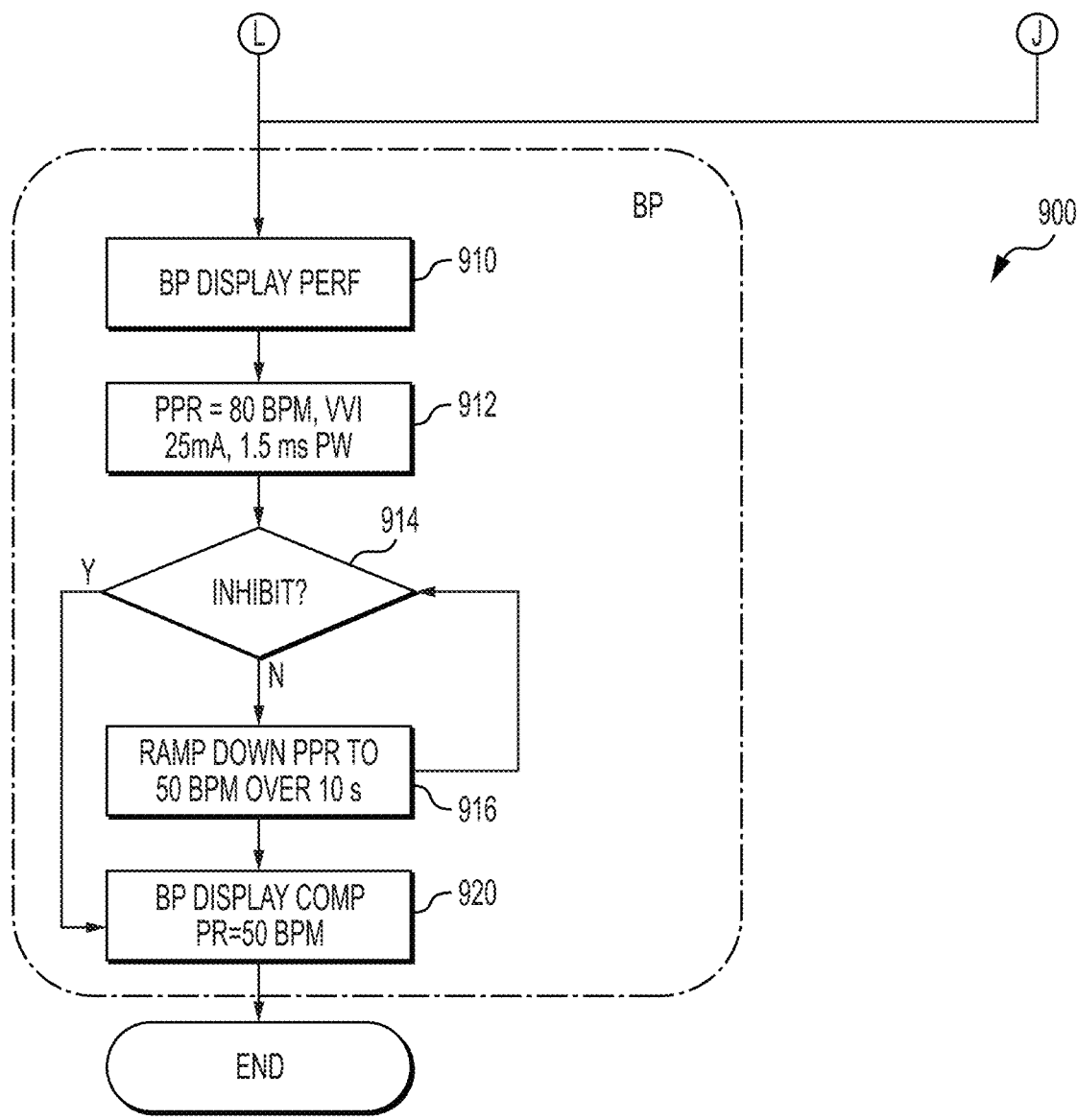

FIG. 13 is a flow chart illustrating a BP process 900 according to an example embodiment, wherein the PPR is automatically ramped down until intrinsic pacing is established. BP may start at step 910 where the back-up pacing indicator 226 displays perform status. The PPR may then be set to approximately 80 BPM, VVI mode, with an amplitude of approximately 25 mA and a pulse width of approximately 1.5 ms, for example, in step 912. A determination 912 may then be made to assess whether the pacer is inhibited, suggesting, in VVI mode, that the HR>PPR and that intrinsic pacing has been established. If pacing has not been inhibited, the PPR may be ramped down to approximately 50 BPM over approximately 10 seconds, for example at step 916, periodically determining 914 if pacing has been inhibited. If pacing has been inhibited, the back-up pacing indicator 226 displays complete status, and the PPR may be set to approximately 50 BPM, for example, or turned off after a period of time. If pacing has not been inhibited at approximately 40-50 BMP, an alarm may be triggered indicating that the patient may be experiencing pathologic bradycardia and the process may enter a manual state where the PPR starts at 50 BPM in VVI mode and the up and down buttons may be used for manual pacing control to return to normal HR. At this point, the stages are complete, suggesting an end to the TAVR procedure, but any stage may be restarted as desired.

The bipolar pacing of a self-expandable valve mode 534 may involve the same or similar to steps involved in mode 532 with the following exceptions. When initiated by the RCM 300, the EPG 200 may pace at approximately 25 mA, approximately 1.5 ms pulse width, and a PPR of approximately 120 BPM, for example. If PVCs are detected, the EPG 200 may increment PPR by 15 BPM every 500 ms seconds until there are no PVCs or the HR reaches 150 BPM. This may be accomplished automatically by the algorithm or triggered by pressing the up button 310 on the RCM 300.

The unipolar pacing of a balloon-expandable valve mode 536, and the unipolar pacing of a self-expandable valve mode 538 may involve the same or similar to steps involved in mode 532 with the following exceptions. When a grounding pad 60 is plugged into EPG 200, the EPG 200 may reconfigure the outputs such that the anode signal is connected to both outputs to the lead 20 and the cathode signal is connected to the grounding pad 60. The grounding pad 60 may be placed over the apex of the heart on the chest wall, for example. The same steps may be executed but CC may be run at 12 mA and 1.5 ms pulse width.

According to embodiments of the disclosed subject matter, an EPG (e.g., EPG 200) described herein may be used for temporary or single-use pacing in clinical settings outside an interventional lab. Such settings may include, but are not limited to, post cardiac surgery settings with surgically placed leads, or in an emergency department or intensive care unit (ICU) for single chamber temporary leads (e.g., right ventricle (RV) leads). Alternatively, or in addition, an EPG disclosed herein may be used for percutaneous pacing for acute heart block, for example, based on a superficial sensing algorithm. Traditional EPGs do not apply intelligence with respect to sensing and/or pacing. An EPG disclosed herein may be implemented using smart pacing functionality to augment a user experience of temporary or single-use pacing outside an interventional lab, and may be used without an RCM (e.g., RCM 300). An EPG disclosed herein may be configured to include one or more inputs and one or more outputs for connection to an ECG lead cable for connection to a plurality (e.g., five) of leads. Such a configuration may provide the capacity for capture detection and pacing (e.g., two outputs to connect to a pacing lead for both atrial and ventricular leads). Such an EPG may have minimal controls for simplicity, and may include a pacer on/off toggle, manual override heartrate up and down controls, and/or a display for displaying a pacing rate.

According to embodiments of the disclosed subject matter, an EPG (e.g., EPG 200) described herein may sense ECG and/or EGM signals and may detect fiducials of a Q wave, R wave, and S wave (QRS) complex such as detection of an R wave. An EPG disclosed herein may also indicate, for example, on a display, a set sensing threshold (e.g., a sensing setting) and may indicate a margin above the sensing threshold. The sensing threshold may include or may be based on an auto sense feature to manage the risk of over sensing and/or under sensing. Such a risk may be managed, for example, as the signal to noise ratio changes in a more subacute implantation of a temporary or single-use lead. Such a risk may be present, for example, over a range of time (e.g., hours or days). Sensing detection disclosed herein may be implemented continuously. Based on the continuous sensing, one or more metrics may be generated. For example, a metric based on an R wave height, or A wave height with respect to the atrial channel, may be plotted over time. Alternatively, or in addition, if a lead has access to multiple bipoles (e.g., based on multiple connections), the EPG may apply an algorithm (e.g., using code, as disclosed herein) to simultaneously assess all or a plurality of the bipoles and to select the bipoles with the highest measured R or A waves or those above a threshold, with the lowest signal to noise ratio or a signal to noise ration below a threshold. Such selected bipoles may be used for sensing and pacing. All or a plurality of the bipoles may be assessed periodically, or when there is a substantive change in R or A wave height, to select a different bipole. Changes in tissue contact or lead fibrosis may trigger different bipoles being selected over time. Such selection to shift sensing and pacing sites may optimize pacemaker function.

According to embodiments of the disclosed subject matter, an EPG (e.g., EPG 200) described herein may perform a pacing threshold test (e.g., percutaneous capture or EGM capture) to determine the quality of pacing and lead contact. An EPG disclosed herein may indicate, for example, on a display, an indication or the results of the last performed pacing threshold test and may also indicate one or more current lead thresholds. The pacing threshold test may be performed automatically on based on a schedule (e.g., a scheduled defined by a user). According to an embodiment, alert levels may be set (e.g., defined by a user), where the alert levels are based on pacing threshold that defines failure in isolation. Alternatively, or in addition, a pacing threshold may be tracked over time, and an increase in pacing threshold (e.g., by a pre-set value or percentage) may be used to alert a user of a potential impending problem with a lead position.

Embodiments Disclosed Herein Include:

1. A system for assisted pacing during a transcatheter heart valve replacement (TAVR) procedure, wherein a heart valve is deployed in a heart paced via a lead positioned in the heart, the system comprising:

an external pulse generator (EPG) configured for connection to the lead; and a remote-control module (RCM) wirelessly connected to the EPG, wherein the RCM includes user inputs configured to control the EPG.

2. A system as in embodiment 1, wherein the lead comprises a guidewire with at least a partial insulative outer portion, the system further including a guidewire connector connected to the EPG via a cable, the guidewire connector configured to penetrate the insulative outer portion to establish electrical communication with the guidewire.

3. A system as in embodiment 1, further comprising:

a central processing unit (CPU) with a memory unit for storing code and a processor for executing the code, wherein the CPU is operably connected to the EPG and RCM;

wherein the code includes instructions to control the EPG based on user input from the RCM.

4. A system as in embodiment 3, wherein the CPU is disposed in the EPG.

5. A system as in embodiment 3, wherein the CPU is disposed in the RCM.

6. A system as in embodiment 3, further comprising an interface module (IM) to facilitate communication between the EPG and RCM.

7. A system as in embodiment 6, wherein the CPU is disposed in the IM.

8. A system as in embodiment 3, wherein the code includes instructions to perform a rapid pacing (RP) routine based on user input from the RCM.

9. A system as in embodiment 8, wherein the RP routine includes the steps of waiting for a user readiness input from the RCM, ramping up a paced pulse rate (PPR) of a pacing output from the EPG, and triggering an indicator when the PPR is suitable for valve deployment.

10. A system as in embodiment 9, wherein the RP routine further includes an automatic PPR ramp up subroutine and an automatic ramp down subroutine.

11. A system as in embodiment 8, wherein the code further includes instructions to perform a continuity test (CT) routine based on user input from the RCM.

12. A system as in embodiment 11, wherein the code further includes instructions to perform a capture check (CC) routine based on user input from the RCM.

13. A system as in embodiment 12, wherein the CC routine includes the steps of waiting for a user readiness input from the RCM, ramping up a pacing output from the EPG, determining if a sensed heart-rate (HR) is the same as the PPR, and triggering an indicator indicative of 1:1 capture.

14. A system as in embodiment 13, wherein the CC routine further includes an automatic rate determination subroutine.

15. A system as in embodiment 13, wherein the CC routine further includes a manual capture rate determination subroutine.

16. A system as in embodiment 13, wherein the CC routine further includes a capture verification subroutine.

17. A system as in embodiment 16, wherein the capture verification subroutine monitors capture over a period corresponding to at least one respiratory cycle.

18. A system as in embodiment 12, wherein the code further includes instructions to perform a back-up pacing (BP) routine based on user input from the RCM.

19. A system as in embodiment 18, wherein the BP routine includes the steps of waiting for a user readiness input from the RCM, ramping down a pacing output from the EPG, determining if a heart-rate (HR) is inhibited, and triggering an indicator indicative of inhibition.

20. A method of temporary cardiac pacing during a transcatheter heart valve replacement (TAVR) procedure wherein a heart valve is deployed via a guidewire, the method comprising:

connecting an external pulse generator (EPG) to the guidewire;

connecting a remote-control module (RCM) to the EPG;

activating a computer executable code based on a user input from the RCM; and executing code instructions to perform a rapid pacing (RP) routine based on the user input from the RCM.

21. A method as in embodiment 20, wherein executing the instructions to perform the RP routine includes the steps of waiting for a user readiness input from the RCM, ramping up a paced pulse rate (PPR) of a pacing output from the EPG, and triggering an indicator when the PPR is suitable for valve deployment.

22. A method as in embodiment 21, wherein executing the instructions to perform the RP routine includes the step of automatically ramping up PPR.

23. A method as in embodiment 22, wherein executing the instructions to perform the RP routine includes the step of automatically ramping down PPR.

24. A method as in embodiment 21, further comprising executing code instructions to perform a continuity test (CT) routine based on user input from the RCM.

25. A method as in embodiment 24, further comprising executing code instructions to perform a capture check (CC) routine based on user input from the RCM.

26. A method as in embodiment 25, wherein executing the instructions to perform the CC routine includes the steps of waiting for a user readiness input from the RCM, ramping up the PPR of the pacing output from the EPG, determining if a sensed heart-rate (HR) is the same as the pacing output, and triggering an indicator indicative of 1:1 capture.

27. A method as in embodiment 26, wherein executing the instructions to perform the CC routine includes the step of automatically determining capture rate.

28. A method as in embodiment 26, wherein executing the instructions to perform the CC routine includes the step of manually determining capture rate.

29. A method as in embodiment 26, wherein executing the instructions to perform the CC routine includes the step verifying 1:1 capture.

30. A method as in embodiment 29, wherein the step of verifying capture is performed over a period corresponding to at least one respiratory cycle.

31. A method as in embodiment 25, further comprising executing code instructions to perform a back-up pacing (BP) routine based on user input from the RCM.

32. A method as in embodiment 31, wherein executing the instructions to perform the BP routine includes the steps of waiting for a user readiness input from the RCM, ramping down the PPR of the pacing output from the EPG, determining if a heart-rate (HR) is inhibited, and triggering an indicator indicative of inhibition.

All of the aspects described in the present disclosure (including references incorporated by reference, accompanying claims, abstract and drawings), may be combined in any order, in part or in full, or in any combination or modification, except when such are incompatible or inconsistent. Furthermore, each aspect may be replaced by alternative features serving the same, equivalent or similar purpose, unless expressly stated otherwise or inconsistent with the teachings herein. Thus, unless expressly stated otherwise, each aspect disclosed herein may be only an example of equivalent or similar features. It is intended that the invention be defined by the attached claims and their legal equivalents.

What is claimed is:

1. A system for cardiac pacing, the system comprising:
an external pulse generator (EPG) configured to connect to an intracardiac lead and to provide pacing outputs;
a remote-control module (RCM) wirelessly connected to the EPG, wherein the RCM is configured to receive user inputs and to control the EPG; and
a central processing unit (CPU) operably connected to the EPG and RCM, the CPU including code having instructions, wherein the CPU is configured to execute the code to perform a rapid pacing (RP) routine in response to a first user input, of the user inputs, received at the RCM, the RP routine comprising:
receiving the first user input from the RCM;
modifying a paced pulse rate (PPR) of a pacing output, of the pacing outputs, from the EPG in response to the first user input, wherein modifying the PPR elevates a heart-rate (HR) above an intrinsic HR;
determining if the modified PPR meets a predetermined setting for elevating the HR above the intrinsic HR; and
generating a first indicator indicating that the modified PPR meets the predetermined setting, when the modified PPR is determined to meet the predetermined setting; and
wherein the CPU is further configured to execute the code to perform a capture check (CC) routine in response to a second user input, of the user inputs, received at the RCM, the CC routine comprising:
receiving the second user input from the RCM;
ramping up the PPR of the pacing output from the EPG to a ramped up PPR in response to receiving the second user input;
receiving a sensed HR;
determining if the sensed HR is approximately the same as the ramped up PPR; and
generating a second indicator, the second indicator indicative of a 1:1 capture in response to determining if the sensed HR is approximately the same as the ramped up PPR of the pacing output.

2. The system of claim 1, wherein the RP routine further comprises an automatic PPR ramp up subroutine.

3. The system of claim 1, wherein the CPU is further configured to execute the code to perform a continuity test (CT) routine, the CT routine comprising:
determining that the intracardiac lead is connected to the EPG; and
generating a third indicator indicating that the intracardiac lead is connected to the EPG, when the intracardiac lead is determined to be connected to the EPG.

4. The system of claim 3, further comprising disabling one or more accessory buttons in response to determining that the intracardiac lead is connected to the EPG.

5. The system of claim 1, wherein the CC routine further includes an automatic rate determination subroutine.

6. The system of claim 1, wherein the CC routine further includes at least one of a manual capture rate determination subroutine or a capture verification subroutine.

7. The system of claim 6, wherein the capture verification subroutine monitors capture over a period of at least one respiratory cycle.

8. The system of claim 1, wherein the CPU is further configured to execute the code to perform a back-up pacing (BP) routine in response to a third user input received at the RCM, the BP routine comprising:
receiving the third user input from the RCM;
ramping down the PPR from the EPG in response to receiving the third user input;
determining if an HR is inhibited; and
generating a third indicator indicative of inhibition in response to determining if the HR is inhibited.

9. The system of claim 1, wherein the EPG is a non-sterile component and the RCM is a sterile component.

10. The system of claim 1, wherein the EPG is configured to transmit pacing output information to a lab display.

11. The system of claim 1, wherein the EPG is configured to operate in either unipolar or bipolar modes of operation.

12. The system of claim 1, wherein the EPG is further configured for connection to a grounding pad.

13. The system of claim 1, wherein the EPG is configured to receive sensing signals from the lead.

14. The system of claim 1, wherein the EPG is configured to receive an electrocardiogram (ECG) signal.

15. The system of claim 1, wherein the system further comprises a guidewire connector connected to the EPG, the guidewire connector being configured to penetrate a partial insulative outer portion of the intracardiac lead to establish electrical communication with a guidewire of the intracardiac lead.

16. The system of claim 1, wherein the CPU is disposed in the EPG or the RCM.

17. The system of claim 1, further comprising an interface module (IM) configured to facilitate communication between the EPG and RCM.

18. The system of claim 17, wherein the CPU is disposed in the IM.

* * * * *